United States Patent
Onishi

(10) Patent No.: US 9,621,777 B2
(45) Date of Patent: Apr. 11, 2017

(54) COMPONENT IMAGING DEVICE, AND COMPONENT MOUNTING DEVICE EQUIPPED WITH COMPONENT IMAGING DEVICE

(71) Applicant: YAMAHA HATSUDOKI KABUSHIKI KAISHA, Shizuoka-ken (JP)

(72) Inventor: Tadashi Onishi, Shizuoka-ken (JP)

(73) Assignee: YAMAHA HATSUDOKI KABUSHIKI KAISHA, Shizuoka-ken (JP)

( * ) Notice: Subject to any disclaimer, the term of this patent is extended or adjusted under 35 U.S.C. 154(b) by 299 days.

(21) Appl. No.: 14/367,723

(22) PCT Filed: Nov. 26, 2012

(86) PCT No.: PCT/JP2012/007574
§ 371 (c)(1),
(2) Date: Jun. 20, 2014

(87) PCT Pub. No.: WO2013/094124
PCT Pub. Date: Jun. 27, 2013

(65) Prior Publication Data
US 2015/0215510 A1     Jul. 30, 2015

(30) Foreign Application Priority Data
Dec. 22, 2011 (JP) .................... 2011-282038

(51) Int. Cl.
*H04N 5/225* (2006.01)
*H05K 13/04* (2006.01)
(Continued)

(52) U.S. Cl.
CPC ......... *H04N 5/2258* (2013.01); *H04N 5/2253* (2013.01); *H04N 5/2254* (2013.01);
(Continued)

(58) Field of Classification Search
CPC .. H05K 13/08; H05K 3/3436; H05K 13/0469; H05K 3/305; H05K 3/0097;
(Continued)

(56) References Cited

U.S. PATENT DOCUMENTS

| 4,675,993 A * | 6/1987 | Harada | G05B 19/4083 228/105 |
|---|---|---|---|
| 7,219,787 B2 * | 5/2007 | Kabeshita | H05K 13/0061 198/345.3 |

(Continued)

FOREIGN PATENT DOCUMENTS

| CN | 1578618 A | 2/2005 |
|---|---|---|
| DE | 11 2008 001925 T5 | 7/2010 |

(Continued)

OTHER PUBLICATIONS

International Search Report; PCT/JP2012/007574; Feb. 26, 2013.
(Continued)

*Primary Examiner* — Dramos I Kalapodas
(74) *Attorney, Agent, or Firm* — Studebaker & Brackett PC

(57) ABSTRACT

A component imaging device has: a head unit that has a first head row and a second head row; an imaging unit that images components held by heads; a moving device for moving the head unit; and an imaging control device. The imaging unit includes an image sensor and an optical system. The optical system includes a first light-guiding portion that guides light from a component of the first head row to the image sensor, and a second light-guiding portion that guides light from a component of the second head row to the image sensor. An optical path length of the first light-guiding portion is set so as to obtain a focused image, and an optical path length of the second light-guiding portion is set so as to obtain a focused image. The imaging (Continued)

control device controls the positions of the heads and the exposure timing.

7 Claims, 13 Drawing Sheets

(51) Int. Cl.
*H04N 5/235* (2006.01)
*H04N 5/238* (2006.01)
*H05K 13/08* (2006.01)
*H04N 7/18* (2006.01)
*G01N 21/956* (2006.01)

(52) U.S. Cl.
CPC ........... *H04N 5/2256* (2013.01); *H04N 5/238* (2013.01); *H04N 5/2355* (2013.01); *H05K 13/0452* (2013.01); *H05K 13/08* (2013.01); *G01N 21/95684* (2013.01)

(58) Field of Classification Search
CPC .............. H05K 3/1216; H05K 13/0452; Y10T 29/53261; Y10T 29/49144; Y10T 29/53183; Y10T 29/5313; Y10T 29/53187; Y10T 29/53178; G02B 3/0037; H04N 5/2254; H04N 5/2256; H04N 5/2258; H04N 5/238; H04N 5/2355; H04N 5/2253; G01N 21/95684
See application file for complete search history.

(56) References Cited

U.S. PATENT DOCUMENTS

| | | | | |
|---|---|---|---|---|
| 7,827,677 B2* | 11/2010 | Ueno | ................ | H01L 21/67144 29/739 |
| 2003/0110610 A1* | 6/2003 | Duquette | ........... | H04N 13/0207 29/407.09 |
| 2004/0033128 A1* | 2/2004 | Kabeshita | .......... | H05K 13/0061 29/740 |
| 2005/0072831 A1* | 4/2005 | Haji | ........................ | H01L 24/81 228/102 |
| 2005/0115060 A1* | 6/2005 | Kondo | ............... | H05K 13/0061 29/650 |
| 2005/0235489 A1* | 10/2005 | Okuda | ............... | H05K 13/0413 29/832 |
| 2006/0062259 A1* | 3/2006 | Delpiano | .................. | G01J 9/00 372/9 |
| 2009/0064489 A1* | 3/2009 | Inoue | ................... | H05K 3/3484 29/739 |
| 2009/0119904 A1* | 5/2009 | Yamasaki | .......... | H05K 13/0408 29/593 |
| 2010/0122455 A1* | 5/2010 | Noda | ................ | H01L 21/67144 29/832 |
| 2010/0152877 A1* | 6/2010 | Maenishi | .......... | H05K 13/0452 700/108 |
| 2010/0321487 A1* | 12/2010 | Endo | ................... | H05K 13/0413 348/87 |
| 2011/0197437 A1* | 8/2011 | Nagao | ..................... | H05K 13/08 29/729 |
| 2011/0243456 A1* | 10/2011 | Kawai | .................. | G06K 9/6253 382/203 |
| 2013/0162808 A1* | 6/2013 | Minamide | ................ | H04N 7/18 348/87 |

FOREIGN PATENT DOCUMENTS

| | | |
|---|---|---|
| EP | 1726913 A1 | 11/2006 |
| JP | 62-179602 A | 8/1987 |
| JP | 2004-356139 A | 12/2004 |
| JP | 2005-049629 A | 2/2005 |
| JP | 2005-347412 A | 12/2005 |
| JP | 2008-010700 A | 1/2008 |
| JP | 2009-164469 A | 7/2009 |

OTHER PUBLICATIONS

The extended European search report issued by the European Patent Office on Jun. 5, 2015, which corresponds to European Patent Application No. 12860718.1-1803 and is related to U.S. Appl. No. 14/367,723.

* cited by examiner

FIG. 12
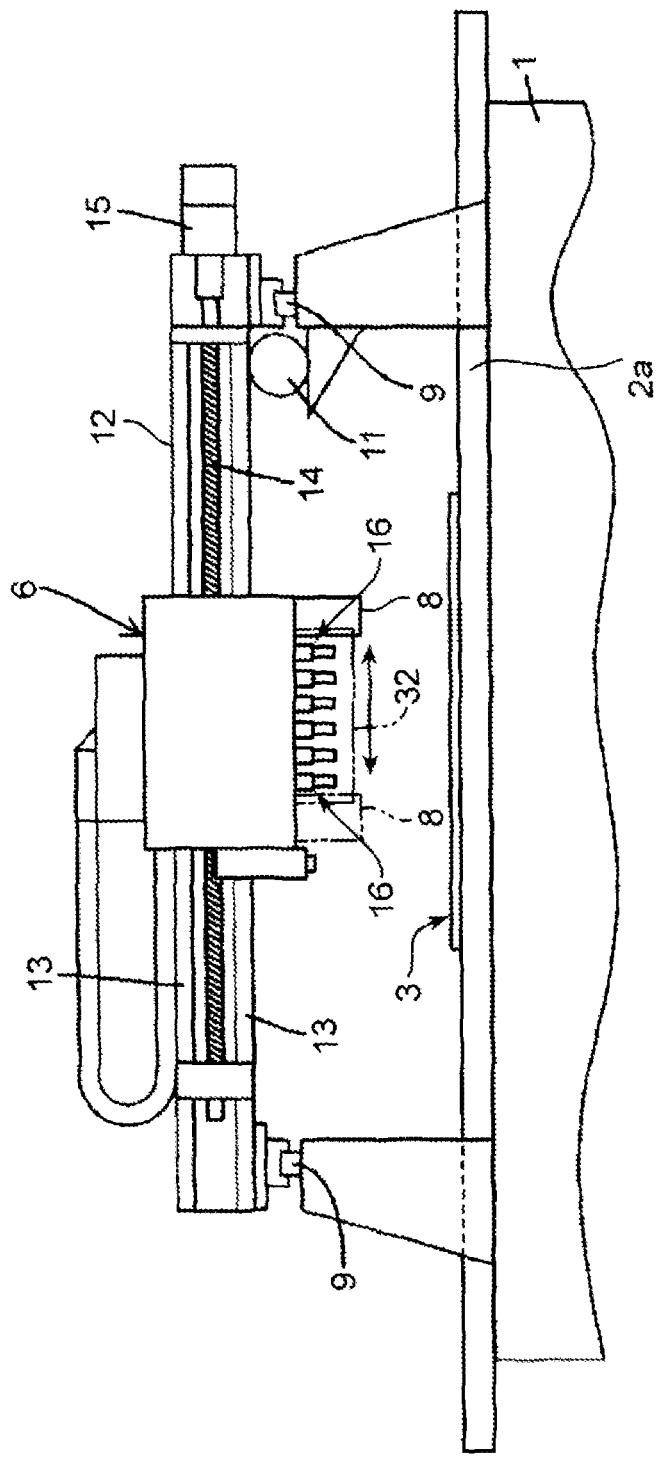
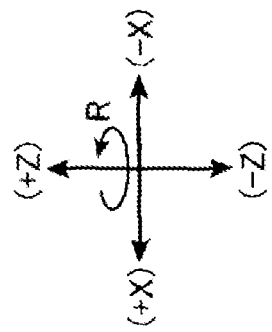

COMPONENT IMAGING DEVICE, AND COMPONENT MOUNTING DEVICE EQUIPPED WITH COMPONENT IMAGING DEVICE

CROSS REFERENCE TO RELATED APPLICATIONS

This application claims benefit of priority to Japanese Patent Application No. 2011-282038 filed Dec. 22, 2011, and to International Patent Application No. PCT/JP2012/007574 filed on Nov. 26, 2012, the entire content of each of which is incorporated herein by reference.

TECHNICAL FIELD

The present technical field relates to a component imaging device that images a component, held by a head, from the side thereof, and a component mounting device equipped with the component imaging device.

BACKGROUND

A component mounting device which extracts a component from a component supply portion and mounts the component on a mounting position on the substrate using a component mounting head has been known. As this type of component mounting device, a device that recognizes a state of the head holding a component in advance prior to mounting the component on the substrate, by imaging the component held by the head from the side thereof, is known. For example, Japanese Patent Application Laid-Open No. 2005-347412 discloses a component mounting device including a head unit where a plurality of mounting heads are disposed in a line, wherein an illumination device that irradiates illumination light onto a component held by each head from the side is equipped in the head unit, and a camera is fixed to a support member that supports the head unit. In this component mounting device, a projection image of a component held by each head is imaged by the camera while the head unit is moving with respect to the support member, and the state of each head holding the component is recognized based on this image.

Lately a number of heads disposed in the head unit tends to increase in order to make the mounting operation more efficient. In this case, a plurality of heads separated into a plurality of rows may be disposed in the head unit, such as an arrangement of a front row and a rear row, in order to prevent the head unit from becoming large.

However if the plurality of heads are arranged in a front row and a rear row, the components held by the heads, which are lined up in the front and rear rows, overlap with each other, which makes it difficult to capture the projection image of each component.

In this case, components of the respective heads arranged in the front and rear rows could be imaged from the side by mutually shifting the locations of the heads in each row, but if the component held by the respective heads are imaged by the same camera (image sensor) simply shift the heads of each row, the distance between each head of the camera becomes different depending on the row, which makes it difficult to image all the components held by the heads with equal image quality.

SUMMARY

It is an object of the present disclosure that when a plurality of component mounting heads, arranged into a plurality of rows, are disposed in a head unit, components held by the respective heads are imaged from the side thereof with equally good quality.

A component imaging device according to an aspect of the present disclosure has: a head unit that has a first head row that includes a plurality of vertically movable heads arranged in a row in a first direction, and a second head row that includes a plurality of vertically movable heads arranged in a row in the first direction and that is arranged in a second direction perpendicular to the first direction with respect to the first head row; an imaging unit that images components held by the respective heads from a position on one side of the second direction; an illumination device for irradiating illumination light for imaging on the components held by the heads; a moving device for relatively moving the head unit with respect to the imaging unit along a predetermined path which is parallel with the first direction, in order to image the components held by the heads; and an imaging control device for performing control related to the component imaging operation, wherein the imaging unit includes an image sensor and an optical system that guides light from a component held by the head for generating an image of the component, to the image sensor. The optical system includes: a first light-guiding portion that guides, to the image sensor, light from a component that has reached a predetermined first component imaging position, out of the components held by the respective heads of the first head row, as the head unit relatively moves along the predetermined path with respect to the imaging unit; and a second light-guiding portion that guides, to the image sensor, light from a component that has reached a predetermined second component imaging position, out of the components held by the respective heads of the second head row. An optical path length from the first component imaging position to the image sensor is set for the first light-guiding portion so as to obtain a focused image of a component held by a head of the first head row. An optical path length from the second component imaging position to the image sensor is set for the second light-guiding portion so as to obtain a focused image of a component held by a head of the second head row. The imaging control device controls height positions of the heads and an exposure timing of the image sensor based on the respective component imaging positions, so that when the head unit relatively moves along the predetermined path with respect to the imaging unit, light from a component held by a head of the first head row is guided to the image sensor by the first light-guiding portion, and light from a component held by a head of the second head row is guided to the image sensor by the second light-guiding portion.

A component mounting device according to an aspect of the present disclosure is a component mounting device that extracts components from a component supply portion and mounts the components on a substrate, comprising: the component imaging device described above; and a mounting control device for mounting components held by the respective heads of the head unit on a substrate by controlling the moving device described above.

BRIEF DESCRIPTION OF THE DRAWINGS

FIG. 12 is a schematic front view of a component mounting device according to Embodiment 4.

DETAILED DESCRIPTION

Embodiments of the present disclosure will now be described with reference to the accompanying drawings.

Embodiment 1

Figure 1:
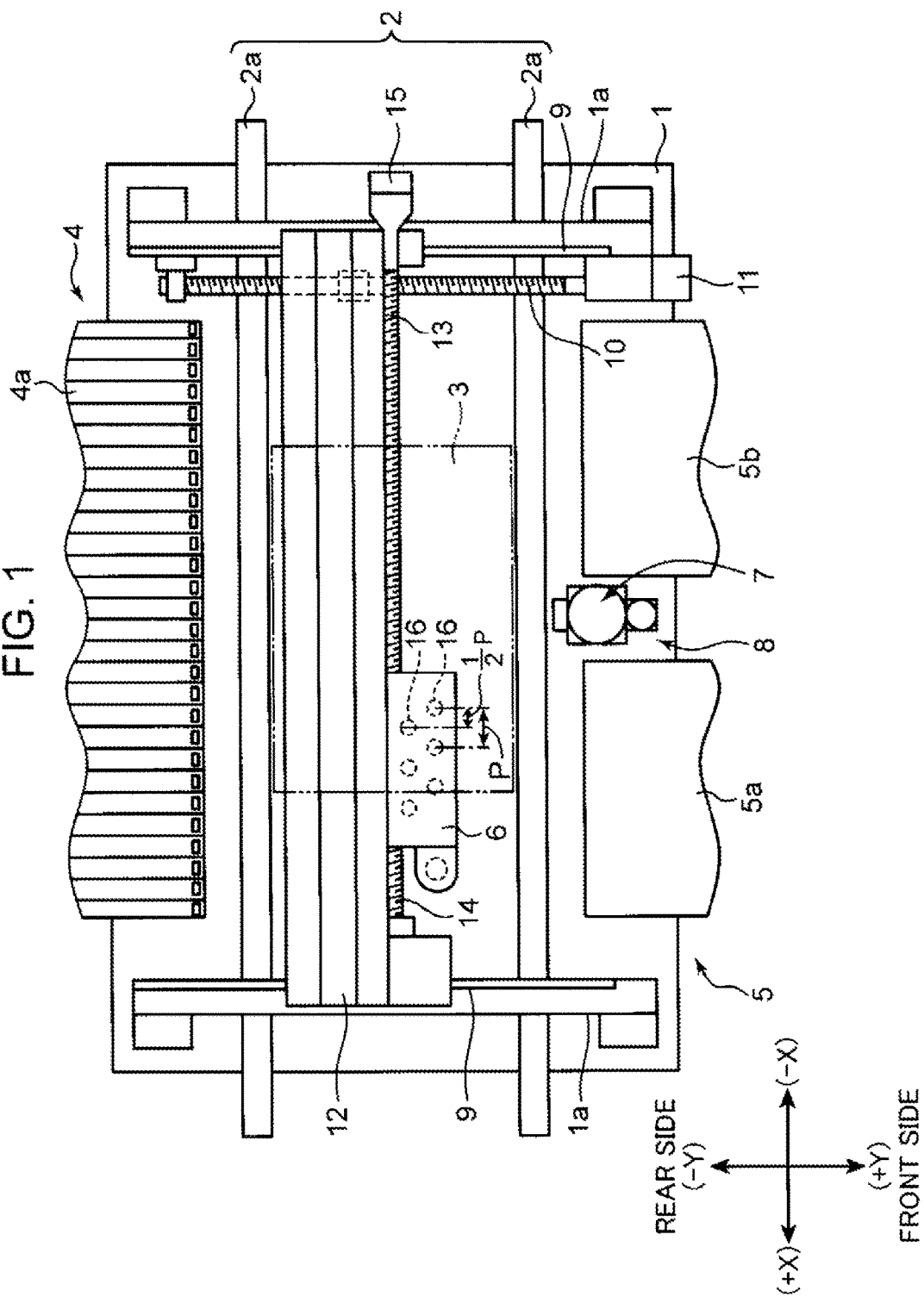
FIG. 1 is a schematic plan view of a component mounting device (component mounting device equipped with the component imaging device according to the present disclosure) according to Embodiment 1 of the present disclosure.
Figure 2:
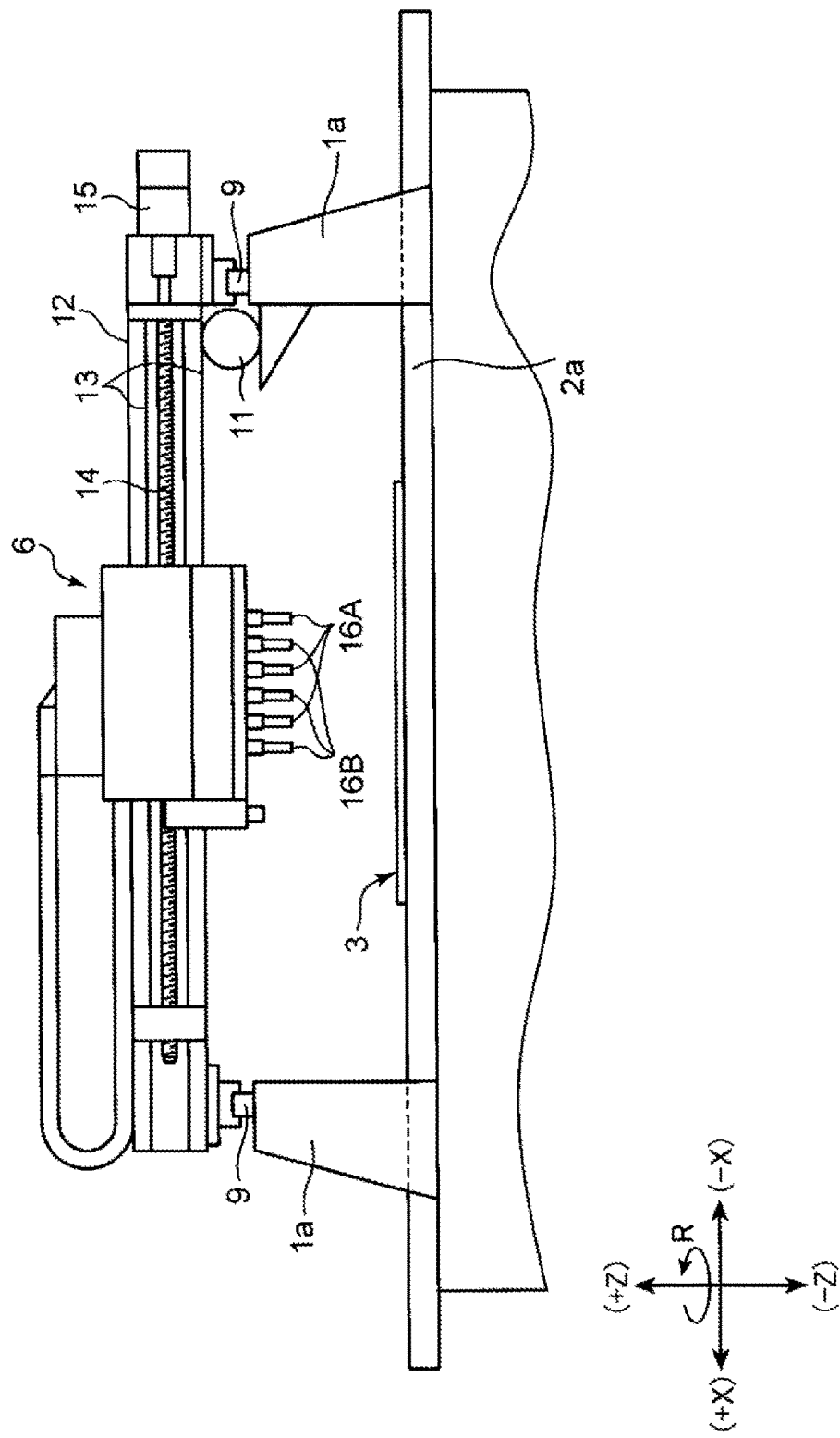
FIG. 2 is a schematic front view of the component mounting device in FIG. 1.

FIG. 1 and FIG. 2 are schematic diagrams of a component mounting device equipped with a component imaging device according to the present disclosure. FIG. 1 is a plan view and FIG. 2 is a front view depicting the component mounting device schematically. In FIG. 1, FIG. 2 and in the drawings to be described later, the rectangular coordinate axes X, Y and Z are shown in order to clarify the directional relationship.

The component mounting device includes a base 1, a substrate transporting mechanism 2 that is disposed on the base 1 and transports a substrate 3, such as a printed wiring board (PWB) in the X direction, component supply portions 4 and 5, a component mounting head unit 6, a head unit driving mechanism for driving the head unit 6, a component imaging unit for recognizing the components held by the head unit 6 and the like.

The substrate transporting mechanism 2 includes a pair of conveyors 2a for transporting the substrate 3 on the base 1. The conveyors 2a receive the substrate 3 from the right side (−X direction) in the drawings, and transport the substrate 3 to a predetermined mounting operation position (position illustrated in the drawings), and hold the substrate 3 there using a holding device (not illustrated). After the mounting operation, the conveyors 2a release holding of the substrate 3 and transport the substrate 3 out to the left side (+X direction side) in the drawings.

The component supply portions 4 and 5 are disposed on both sides of the substrate transporting mechanism 2 (both sides in the Y direction). On the component supply portion 4, which is on the rear side of the device (−Y direction side) out of the component supply portions 4 and 5, a plurality of tape feeders 4a line up in the X direction along the substrate transporting mechanism 2. Each of the tape feeders 4a includes a reel where a tape storing and holding chip components, such as ICs, transistors and capacitors, are wound, and supplies a component to a predetermined component supply position near the substrate transporting mechanism 2 while feeding the tape from the reel intermittently. On the component supply portion 5, which is on the front side of the device (+Y direction side), on the other hand, trays 5a and 5b are set in the X direction at a predetermined interval therebetween. On each tray 5a and 5b, package type components, such as a quad flat package (QFD) and a ball grid array (BGA), are arranged so as to be extracted by the head unit 6 (described later).

The head unit 6 is for extracting components from the component supply portions 4 and 5 and mounting the components on the substrate 3, and is disposed above the substrate transporting mechanism 2 and the component supply portions 4 and 5.

The head unit 6 can be moved in the X direction and the Y direction within a predetermined area by the head unit driving mechanism. The head unit driving mechanism is secured to a pair of elevated frames 1a disposed on the base 1 respectively, and includes a pair of fixed rails 9 which extend parallel in the Y direction, a unit support member 12 which is supported by the fixed rails 9 and extends in the X direction, and a ball screw shaft 10 which is screwed into the unit support member 12, and is driven by the Y axis servo motor 11. The head unit driving mechanism also includes a fixed rail 13 which is secured in the unit support member 12 and supports the head unit 6 so as to be movable in the X direction, and a ball screw shaft 14 which is screwed into the head unit 6 and is driven by the X axis servo motor 15 as a driving source. In other words, the head unit driving mechanism moves the head unit 6 in the X direction via the ball screw shaft 14 by the driving of the X axis servo motor 15, and moves the unit support member 12 in the Y direction via the ball screw shaft 10 by the driving of the Y axis servo motor 11. As a result, the head unit driving mechanism moves the head unit 6 in the X direction and the Y direction within a predetermined area.

The head unit 6 includes a plurality of mounting heads 16 each of which has a nozzle to hold a component by suction at the tip, and a head driving mechanism that uses a servo motor (not illustrated) as a driving source, for ascending/descending the mounting heads 16 with respect to the head unit 6 (movement in the Z direction), and for rotating the mounting heads 16 around the center axis of the nozzle (rotation in the R direction in FIG. 2).

There are a total of six mounting heads 16, which are separated into three heads in a front row and three heads a rear row, and are arranged in the X direction in a line at a predetermined pitch P in each row. In the following description, a row of the mounting heads 16 disposed on the front side of the device is called the "front row" (corresponding to the first head row of the present disclosure), and a row of the mounting heads 16 disposed on the rear side of the device is called the "rear row" (corresponding to the second head row of the present disclosure), and when necessary, the mounting heads 16 of the front row are called the "front row heads 16A", and the mounting heads 16 of the rear row are called the "rear row heads 16B". In this embodiment, the X direction corresponds to the first direction of the present disclosure, and the Y direction corresponds to the second direction of the present disclosure.

The array pitch P of the front row heads 16A and the array pitch P of the rear row heads 16B are the same, and each front row head 16A is a half pitch (½ P) offset in the X (−X) direction with respect to each rear row head 16B. Thereby six mounting heads 16 are arranged in a zigzag manner. To be more specific, when the front row heads 16A and the rear row heads 16B are disposed at the same height positions and viewed in the +Y direction (corresponding to the specific direction of the present disclosure), the six mounting heads 16 are arranged in a zigzag manner so that the components held by the respective mounting heads 16 do not overlap with one another.

A nozzle of each mounting head 16 can be connected to one of a negative pressure generator, a positive pressure generator, and the atmosphere via an electric switching valve. In other words, the nozzle can hold a component by suction by supplying negative pressure to the tip thereof, and release the hold of the component by supplying positive pressure.

The component imaging unit is for imaging the component so as to recognize the holding state of the component extracted from the component supply portions 4 and 5 by the mounting head 16. The component imaging unit is disposed in a position between the trays 5a and 5b on the base 1. In this embodiment, the first and second component imaging units 7 and 8 are disposed as the component imaging units, as shown in FIG. 1 and FIG. 3, and the second component imaging unit 8 corresponds to the component imaging unit of the present disclosure.

Figure 3:
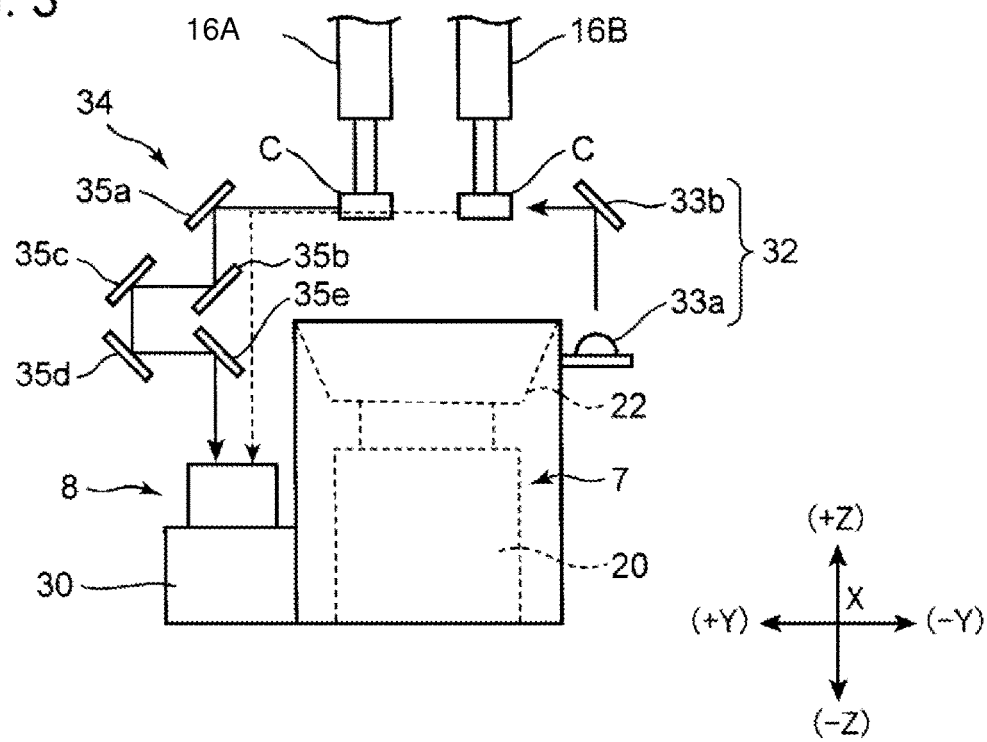
FIG. 3 is a schematic side view of a component imaging unit.

The first component imaging unit 7 is for imaging the components held by the mounting heads 16 mainly from the bottom, and as illustrated in FIG. 3, a component C held by each mounting head 16 (hereafter may be called the "holding component C") is imaged while the head unit 6 (mounting head 16) is relatively moving above the first component imaging unit 7 along a predetermined path parallel with the X direction. The first component imaging unit 7 includes a camera 20 that has a CCD area sensor, a lens or the like, and an illumination portion 22 that has such a light source as an LED to provide illumination light for imaging to the component C, and irradiates the illumination light onto the component C mainly from the bottom, images the reflection image thereof by the camera 20, and outputs the image data to the controller 40, which is described later.

The second component imaging unit 8 images a component C held by each mounting head 16 from the side thereof. The second component imaging unit 8 images the holding component C of each mounting head 16 while the head unit 6 (mounting head 16) moves above the first component imaging unit 7 along the predetermined path.

Figure 4:
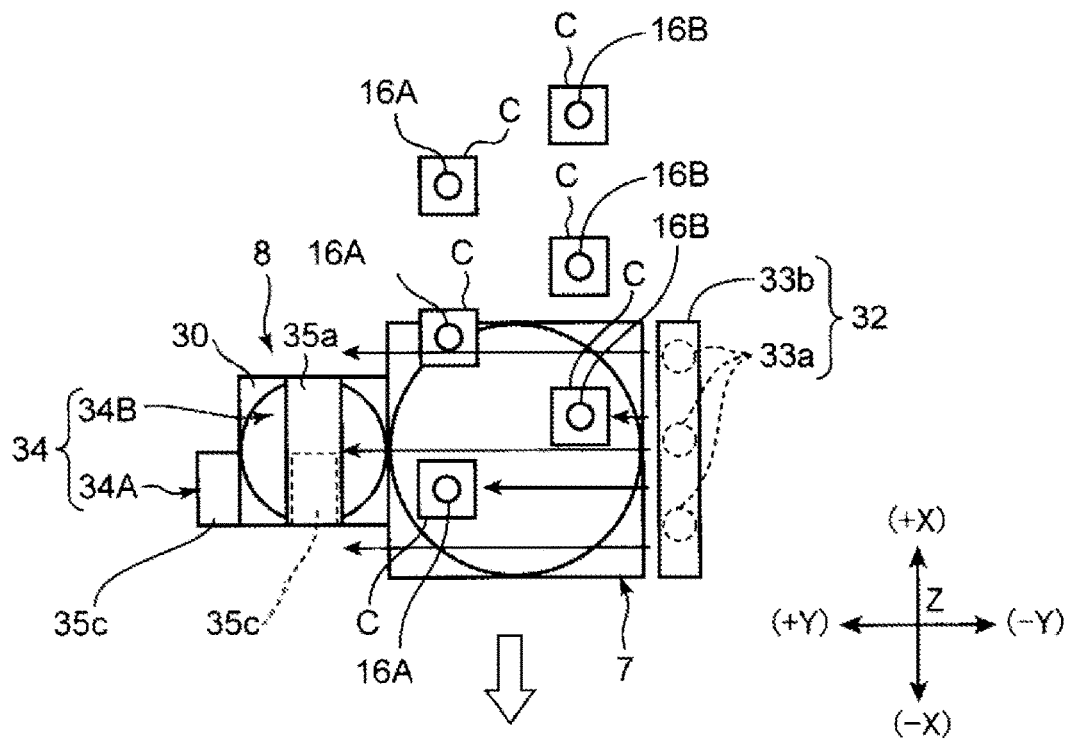
FIG. 4 is a schematic plan view of the component imaging unit.

As illustrated in FIG. 3 and FIG. 4, the second component imaging unit 8 includes a camera 30 that has a CCD area sensor (image sensor), a lens and the like, an illumination portion 32 that provides backlight illumination light to the component C from the side, and an optical system 34 that guides the transmitted light from the periphery of the component (that is, light from the component to generate a projection image of the component) to the camera 30. In this embodiment, the second component imaging unit 8 includes the illumination portion 32 (corresponding to the illumination device of the present disclosure), but the illumination portion 32 may be separated from the second component imaging unit 8.

Out of the second component imaging unit 8, the camera 30 and the optical system 34 are disposed on the front side (+Y direction side) of the first component imaging unit 7, and the illumination portion 32 is disposed on the rear side (−Y direction side) of the first component imaging unit 7. The illumination portion 32 includes a light source 33a, such as an LED, for irradiating illumination light upward, and an illumination mirror 33b that refracts the illumination light at approximately right angles, so as to guide the light to the front side of the device. Because of this configuration, the second component imaging unit 8 irradiates the illumination light onto the component C using the illumination portion 32 in the direction from the rear side to the front side of the device, and guides the projection image thereof to the camera 30 using the optical system 34 so as to capture the image, and outputs the image data from the camera 30 to the controller 40, which is described later.

The illumination portion 32 has an illumination width which allows irradiating the illumination light onto each holding component C of a pair of heads 16A and 16B which are adjacent to each other in the X direction, out of the front row heads 16A and the rear row heads 16B. On the other hand, the optical system 34 simultaneously guides the projection images of the respective holding components C of the heads 16A and 16B to mutually different areas of the camera 30. Thereby the second component imaging unit 8 can simultaneously image the respective holding components C of the pair of heads 16A and 16B which are adjacent to each other in the X direction.

Concerning the optical system 34, the optical system 34 includes a first light-guiding portion 34A and a second light-guiding portion 34B for guiding the projection images of the components C held by the heads 16A and 16B, which are adjacent to each other, to the camera 30 respectively. The light-guiding portions 34A and 34B are disposed in the X direction, and the first light-guiding portion 34A is located on the −X direction side, and the second light-guiding portion 34B is located on the +X direction side. In other words, when a component held by the front row head 16A reaches a predetermined imaging position (called the "first component imaging position" when necessary) as the head unit 6 moves along the predetermined path relative to the second component imaging unit 8, the first light-guiding portion 34A guides the projection image of this component to the camera 30. On the other hand, when a component held by the rear row head 16B reaches an imaging position which has the same height as the imaging position mentioned above and is adjacent to the imaging position in the +X direction (called the "second component imaging position" when necessary), the second light-guiding portion 34B guides the projection image of this component to the camera 30.

The first light-guiding portion 34A and the second light-guiding portion 34B share a first mirror 35a, which reflects the projection images of the respective holding components C of the heads 16A and 16B downward (−Z direction). The first mirror 35a has an elongated shape in the X direction, and reflects the projection images of the respective holding components C of the heads 16A and 16B using mutually different areas in the longitudinal direction. The first light-guiding portion 34A further includes a second mirror 35b to a fifth mirror 35e, which reflect the reflection image by the first mirror 35a a plurality of times (four times in this case) and guide the image downward, in a position corresponding to the half side (half in the −X direction side) in the longitudinal direction of the first mirror 35a. In other words, the first light-guiding portion 34A guides the projection image of the component C to the camera 30 by reflecting the image a plurality of times using the first mirror 35a to the fifth mirror 35e, whereas the second light-guiding portion 34B guides the projection image of the component C to the camera 30 by reflecting the image using only the first mirror 35a. As illustrated in FIG. 4, in the first light-guiding portion 34A, the optical path length from the first component imaging position (position of the holding component C of the front row head 16A) to the camera 30 is set such that the image of the component C is correctly focused, that is, a focused image of the component C is obtained when the holding component C of the front row head 16A is placed in the first component imaging position. In the second light-guiding portion 34B, on the other hand, an optical path length from the second component imaging position (position of the holding component C of the rear row head 16B) to the camera 30 is set such that a focused image of the component C is obtained when the holding component C of the rear row head 16B is placed in the second component imaging position. In other words, these light-guiding portions 34A and 34B are constructed so that the optical path length of the first light-guiding portion 34A, from (the holding component C of) the front row head 16A to the camera 30, and the optical length of the second light-guiding portion 34B, from (the holding component C of) the rear row head 16B to the camera 30, are the same. By this configuration, the second component imaging unit 8 can obtain equal quality focused images for the projection images of all the holding components C of the front row heads 16A and the rear row heads 16B.

In FIG. 3, the solid line indicates an optical path of the projection image of the component C held by the front row head 16A (optical path by the first light-guiding portion 34A), and the broken line indicates an optical path of the projection image of the component C held by the rear row head 16B (optical path by the second light-guiding portion 34B). In FIG. 3, a part of the optical path by the second light-guiding portion 34B (the optical path from the first mirror 35a to the camera 30) actually overlaps with the optical path of the first light-guiding portion 34A (optical path from the first mirror 35a to the second mirror 35b, and the optical path from the fifth mirror 35e to the camera 30), but the optical path by the second light-guiding portion 34B is intentionally shifted in FIG. 3 in order to clearly show the optical path, and therefore in FIG. 3, the optical length of the light-guiding portion 34A and that of the light-guiding portion 34B are not drawn to have the same distance. This shift of the optical paths of the light-guiding portions 34A and 34B in the drawing and the difference of the optical path lengths of the light-guiding portions 34A and 34B seen in the drawing are the same for the embodiments to be described later.

Figure 5:
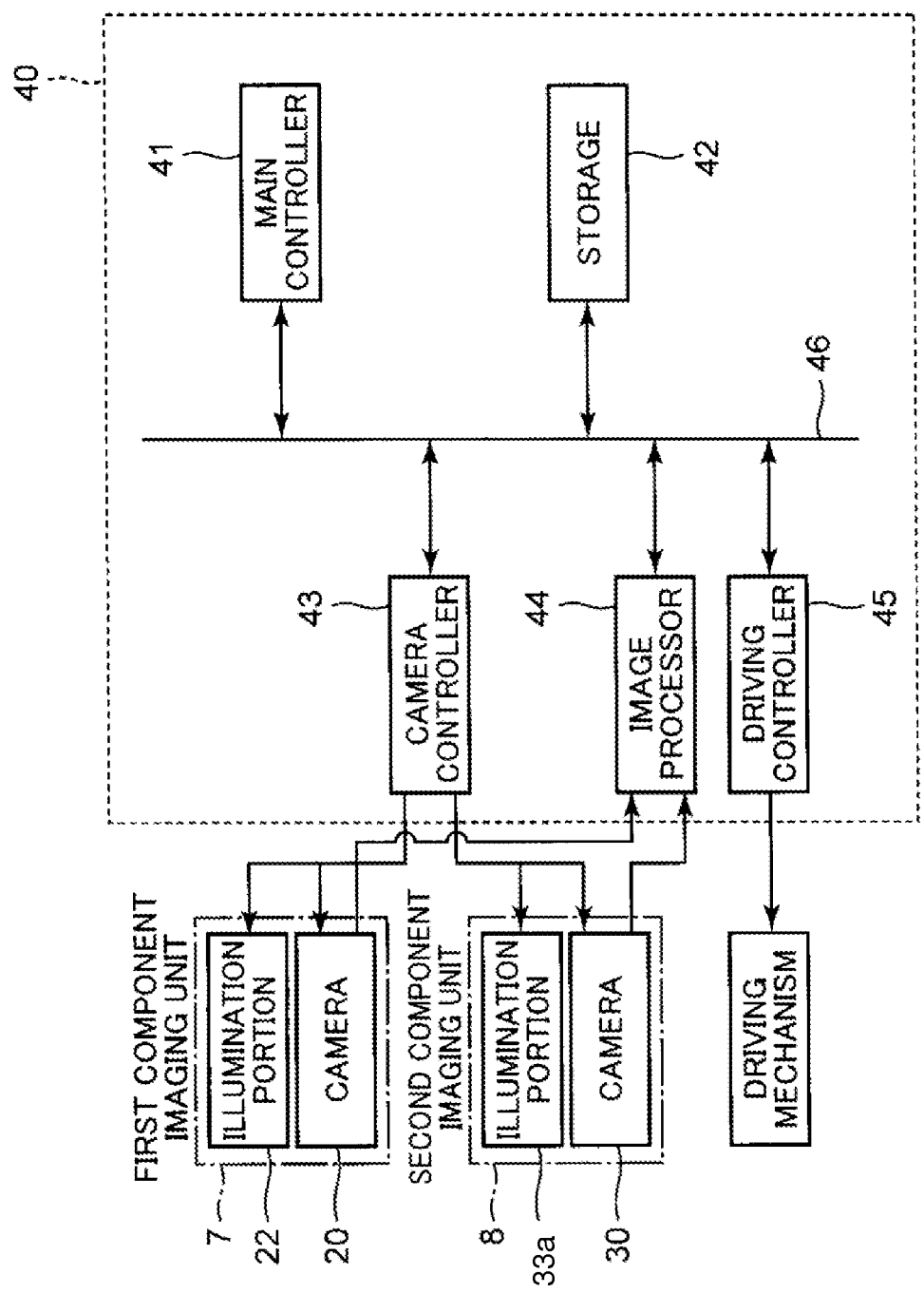
FIG. 5 is a block diagram depicting a control system of the component mounting device.

In order to control the operation comprehensively, the component mounting device further includes a controller 40 depicted in FIG. 5. The controller 40 includes a CPU that executes logical operations, a ROM that stores various programs for controlling the CPU, a RAM that temporarily stores various data, an HDD and other components. As a functional configuration, the controller 40 includes a main controller 41, a storage 42, a camera controller 43, an image processor 44 and a driving controller 45, which are connected such that signals can be exchanged via a bus.

The main controller 41 executes the component mounting operation by comprehensively controlling the head unit driving mechanism, the head driving mechanism and other driving mechanisms via the driving controller 45 according to the mounting programs stored in the storage 42. In particular, after the mounting head 16 descends in the Z direction and extracts the components from the component supply portions 4 and 5, the main controller 41 controls the height positions of the front row heads 16A and the rear row heads 16B and the driving of the head unit 6 using the driving controller 45, and controls the exposure timing of the cameras 20 and 30 in the respective component imaging units 7 and 8 using the camera controller 43.

The image processor 44 performs predetermined image processing on the image data from the cameras 20 and 30, and based on the processed image, the main controller 41 recognizes the component holding state of each mounting head 16. In this embodiment, the head unit driving mechanism corresponds to the moving device of the present disclosure, and the main controller 41, the camera controller 43 and the driving controller 45 correspond to the imaging control device and the mounting control device of the present disclosure.

In this component mounting device, the component mounting operation is performed as follows based on the control by the controller 40. First the head unit 6 moves onto the component supply portions 4 and 5, and the respective mounting heads 16 hold the components by suction. After the components are held by suction, the head unit 6 passes through the first component imaging unit 7 in the X direction (white arrow direction in FIG. 4) along the predetermined path, and during this passing the components held by the respective mounting heads 16 in the front row and the rear row are imaged by the respective imaging units 7 and 8.

To be more specific, after the front row heads 16A and the rear row heads 16B are disposed at predetermined component imaging height positions, so that the holding components C of the respective mounting heads 16 pass through between the illumination portion 32 of the second component imaging unit 8 and the optical system 34 (through the optical path between the illumination mirror 33b and the first mirror 35a) above the first component imaging unit 7, the head unit 6 moves in the X direction at a predetermined speed.

While the head unit 6 (mounting heads 16) is moving, the lighting timing of the illumination portion 22 on the first component imaging unit 7 is controlled so that the illumination portion 22 turns ON at a timing when each component C reaches above the camera 20, whereby each component C is imaged from below by the first component imaging unit 7. Further, as illustrated in FIG. 4, the lighting timing of the illumination portion 32 is controlled (in other words, the exposure timing is controlled) so that the illumination portion 32 turns ON at a timing when a holding component C of the front row head 16A reaches a position corresponding to the first light-guiding portion 34 of the optical system 34 (first component imaging position), and a holding component C of the rear row head 16B reaches a position corresponding to the second light-guiding portion 34B (second component imaging position), whereby projection images of the holding components C held by the adjacent two heads 16A and 16B are captured from the side (+Y direction side) by the second component imaging unit 8. In this case, as mentioned above, in the first light-guiding portion 34A, the optical length is set such that a focused image of the holding component C of the front row head 16A is obtained, and in the second light-guiding portion 34B, the optical length is set such that a focused image of the holding component C of the rear row head 16B is obtained, and hence good focused images can be obtained for any of the heads 16A and 16B.

When imaging of the component C by the component imaging units 7 and 8 completes, the suction state of the components C held by the respective mounting heads 16 (positional shift and inclination of a component with respect to the mounting head 16 in the X direction, Y direction and R direction) and the defects of the components C are recognized by the main controller 41, based on the bottom surface image (reflection image) of each component C imaged by the first component imaging unit 7 and a projection image imaged by the second component imaging unit 8 from the side of each component C. If there is a defective component C or a component in an uncorrectable suction state, among the components C held by the respective mounting heads 16, this component C is registered as a disposal target, and the head unit 6 moves to the position above the substrate 3 and mounts components C other than the disposal target sequentially on the substrate 3. In this case, each component C is appropriately mounted on each placement position of the substrate 3 by the main controller 41, which controls the position of the head unit 6, the rotation angle of the mounting heads 16 or the like using the driving controller 45, so as to correct the suction position error of the component C according to the component recognition result.

When the components C are mounted on the substrate 3 in this way, the head unit 6 moves to the position on the component disposal box (outside the drawings) and disposes the disposal target component C. Thereby one mounting operation cycle completes, and by repeating this operation as necessary, all required components are mounted on the substrate 3.

According to this kind of component mounting device, the head unit 6 can equip many mounting heads 16 to perform the mounting operation of the components C efficiently, and the head unit 6 can be constructed to be compact in the X direction. Furthermore, the projection images of the holding components C of the respective mounting heads 16 arranged in the front row and the rear row can be obtained from the side equally with good quality, and hence components can be efficiently recognized based on the projected images merely by moving the head unit 6 once in one direction with respect to the first component imaging unit 7, just like a conventional device having only one row of mounting heads.

Figure 6:
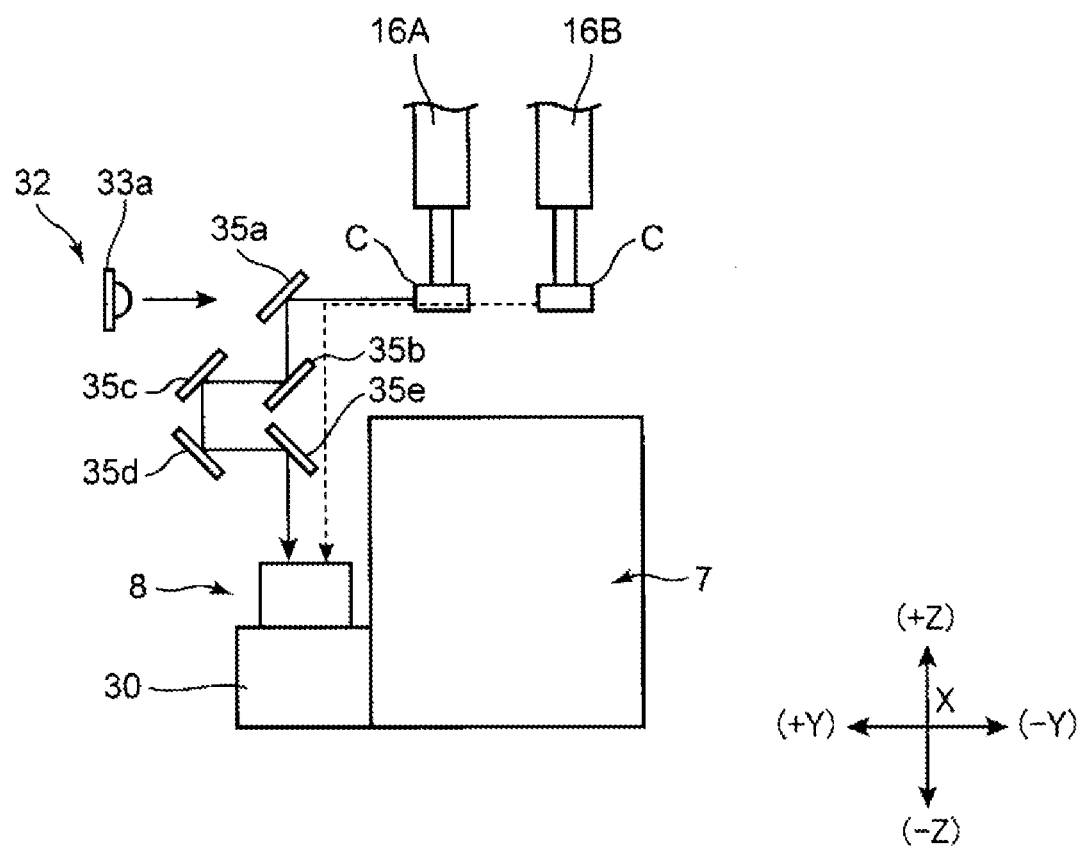
FIG. 6 is a schematic side view of a modification of the component imaging unit.

In this component mounting device, the second component imaging unit 8 captures a projection image of the components C, but may also capture a reflection image of the components C. FIG. 6 is an example of this embodiment. In the second component imaging unit 8 in FIG. 6, the first mirror 35a is a half mirror. The illumination portion 32 is constructed such that the illumination light is directly irradiated onto the holding components C of the respective heads 16A and 16B which are positioned at the same imaging height, from the light source 33a disposed at the same height as the first mirror 35a and on the front side (+Y direction side) of the first mirror 35a, using via the first mirror 35a.

According to this configuration, the illumination light reflected by the holding component C of the front row head 16A (that is, the light from this component to form the reflected image of the component) is reflected by the first mirror 35a to the fifth mirror 35e, and is guided to the camera 30. Further, the illumination light reflected by the holding component C of the rear row head 16B is reflected by the first mirror 35a, and is guided to the camera 30. Thereby the reflection images of the components C held by the respective heads 16A and 16B are imaged by the camera 30 respectively.

Embodiment 2

Figure 7:
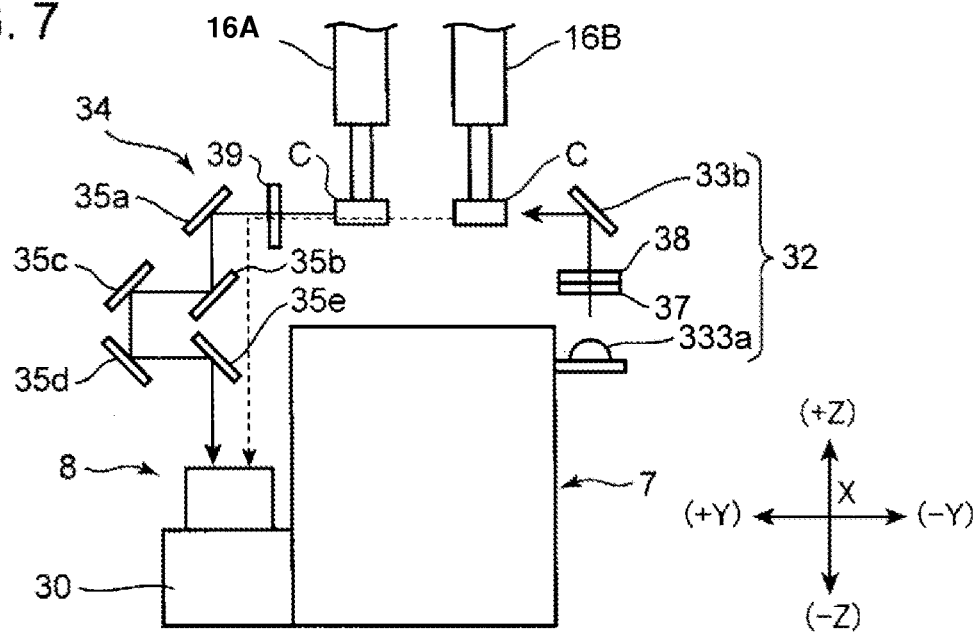
FIG. 7 is a schematic side view of a component imaging unit equipped in a component mounting device according to Embodiment 2.
Figure 8:
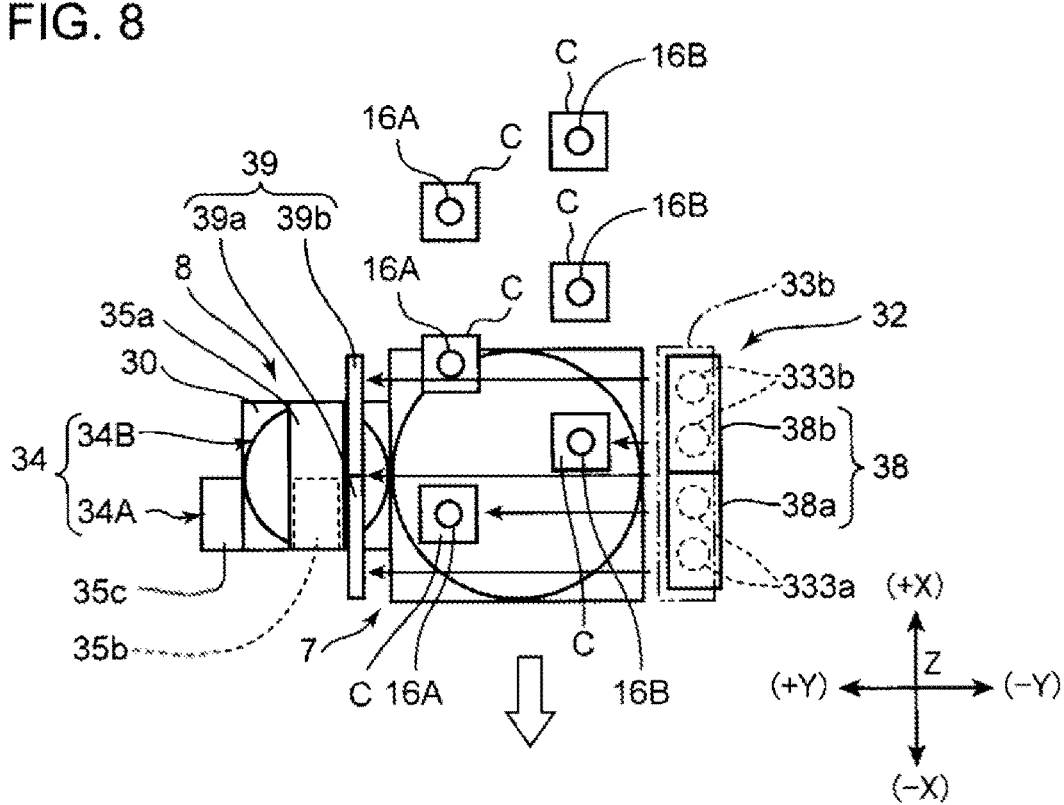
FIG. 8 is a schematic plan view of the component imaging unit.

FIG. 7 and FIG. 8 are schematic diagrams of a component imaging unit of a component mounting device according to Embodiment 2. In the component mounting device, the configuration of the second component imaging unit 8 is different from that of Embodiment 1 in terms of the following aspects, and the rest of the configuration is basically the same as the component mounting device of Embodiment 1. In the following description, a component element which is the same as Embodiment 1 is denoted with the same reference symbol, for which a description is omitted, and primarily a difference from Embodiment 1 will be described.

In the second component imaging unit 8 according to Embodiment 2, the illumination portion 32 includes a first light source 333a that irradiates illumination light having a first wavelength, and a second light source 333b that irradiates illumination light having a second wavelength that is different from the first wavelength. The first light source 333a is disposed on the −X direction side of the center position of the illumination portion 32 in the X direction, and the second light source 333b is disposed on the +X direction side thereof.

The illumination portion 32 also includes a diffusion plate 37 and a light source side optical filter 38. The diffusion plate 37 and the light source side optical filter 38 are disposed between the light sources 333a and 333b and an illumination mirror 33b. The light source side optical filter 38 includes a first light source side filter portion 38a and a second light source side filter portion 38b. As illustrated in FIG. 8, the first light source side filter portion 38a is disposed on the −X direction side of the center position of the light source side optical filter 38 in the X direction, and removes the light components having the second wavelength from the illumination light. The second light source side filter portion 38b is disposed on the +X direction side of the center portion of the light source side optical filter 38 in the X direction, and removes the light components having the first wavelength from the illumination light. Because of this configuration, the illumination portion 32 irradiates the illumination light having the first wavelength to components C on the −X direction side of the center position in the X direction, and irradiates the illumination light having the second wavelength to components C on the +X direction side thereof.

The optical system 34 includes a camera side optical filter 39. The camera side optical filter 39 is disposed between the holding components C of the mounting heads 16 and the first mirror 35a. The camera side optical filter 39 includes a first camera side filter portion 39a and a second camera side filter portion 39b. The first camera side filter portion 39a is disposed on the −X direction side of the center position of the camera side optical filter 39 in the X direction, and allows the light components having the first wavelength to transmit while removing the light components having the second wavelength. The second camera side filter portion 39b is disposed on the +X direction side of the center position of the camera side optical filter 39 in the X direction, and allows the light components having the second wavelength to transmit while removing the light components having the first wavelength.

In the second component imaging unit 8 according to Embodiment 2, the illumination light having the first wavelength is irradiated onto the holding component C of the front row head 16A (corresponding to the first component of the present disclosure), which is disposed in a position corresponding to the first light-guiding portion 34A, as illustrated in FIG. 8. Then the projection image thereof is guided to the camera 30 after the light components having the second wavelength are removed by the camera side optical filter 39 (first camera side filter portion 39a). On the other hand, the illumination light having the second wavelength is irradiated onto the holding component C of the rear row head 16B (corresponding to the second component of the present disclosure), which is disposed in a position corresponding to the second light-guiding portion 34B. Then the projection image thereof is guided to the camera 30 after the light components having the first wavelength are removed by the camera side optical filter 39 (second camera side filter portion 39b).

According to the second component imaging unit 8 of Embodiment 2, the projection images of the components C held by the adjacent heads 16A and 16B can be captured more clearly. In other words, in the case when the components held by the adjacent heads 16A and 16B are very close to each other, for example, if illumination light, including the light components having the same wavelengths, is irradiated from the illumination portion 32, the illumination light contacts the holding component C of each head 16A and 16B and then scatters, and the scattered light mixes with the projection image of the component C, whereby the contrast of each projection image drops. However according to the second component imaging unit 8 of Embodiment 2, even if the scattered light having the second wavelength that is scattered by contacting the holding component C of the rear row head 16B mixes with the projection image of the holding component C of the front row head 16A, the light components having the second wavelength are removed by the camera side optical filter 39 (first camera side filter portion 39a). For the projection image of the holding component C of the rear row head 16B as well, the light components having the first wavelength are removed by the camera side optical filter 39 (second camera side filter portion 39b). Therefore according to the second component imaging unit 8 of Embodiment 2, the influence of the scattered light can be removed from the projection image of any component C held by each head 16A and 16B. As a consequence, a clear projection image with good contrast can be obtained for any holding component C.

In this embodiment, the light source side optical filter 38 and the camera side optical filter 39 correspond to the filter device of the present disclosure, the first light source side filter portion 38a and the first camera side filter portion 39a correspond to the first filter (the first upstream side filter and the first downstream side filter) of the present disclosure, and the second light source side filter portion 38b and the second camera side filter portion 39b correspond to the second filter (the second upstream side filter and the second downstream side filter) of the present disclosure.

In this embodiment, the second component imaging unit 8 includes both the light source side optical filter 38 and the camera side optical filter 39, but may have a configuration that includes only one of these filters. The second component imaging unit 8 may also have a configuration that includes only one of the first filter (the first light source side filter portion 38a and the first camera side filter portion 39a) and the second filter (the second light source side filter portion 38b and the second camera side filter portion 39b). In other words, it is sufficient that the filter device is appropriately disposed such that the influence of the scattered light is suppressed by removing specific light components, and projection images with good contrast are obtained as the projection images of the components C held by the adjacent heads 16A and 16B.

Instead of using the illumination portion 32 including the light sources 333a and 333b that irradiate illumination light of the light components having mutually different wavelengths, as in the case of this embodiment, general white light sources may be used as the light sources, and a filter device may be placed on each optical path from the light source to the CCD area sensor, so that light including different light components enter the CCD area sensor as projection images of the components C held by the adjacent heads 16A and 16B. For example, the first light source side filter portion 38a disposed on the −X side in FIG. 8 allows the illumination light having the first wavelengths to pass and removes the illumination light having the other wavelengths, so that the illumination light having the first wavelength, out of the illumination light from the white light source, is irradiated onto the holding component C of the front row head 16A. And the second light source side filter portion 38b disposed on the +X side allows the illumination light having the second wavelength to pass and removes the illumination light having the other wavelength, so that the illumination light having the second wavelength, out of the illumination light from the white light source, is irradiated onto the holding component C of the rear row head 16B. On the other hand, the first camera side filter portion 39a disposed on the −X side in FIG. 8 allows the projection image of the light components having the first wavelengths to pass and removes the projection image of the light components having the other wavelengths, so that the projection image of the light components having the first wavelength, out of the light (that is, the projection images) of the holding component C of the front row head 16A, is guided to the camera 30. And the second camera side filter portion 39b disposed on the −X side allows the projection image of the light components having the second wavelength to pass and removes the projection images of the light components having the other wavelengths, so that the projection image of the light components having the second wavelength, out of the projection images of the holding component C of the rear row head 16B, is guided to the camera 30. By this configuration as well, the influence of the scattered light can be suppressed, and images with good contrast can be obtained as projection images of the components C held by the adjacent heads 16A and 16B.

Embodiment 3

Figure 9:
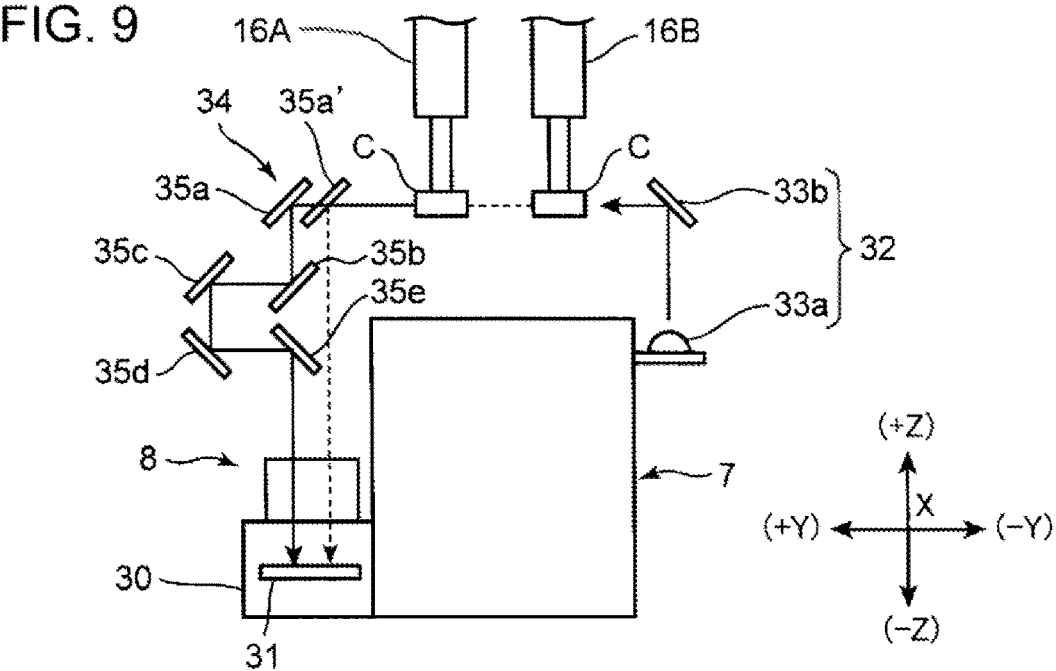
FIG. 9 is a schematic side view of a component imaging unit equipped in a component mounting device according to Embodiment 3.
Figure 10:
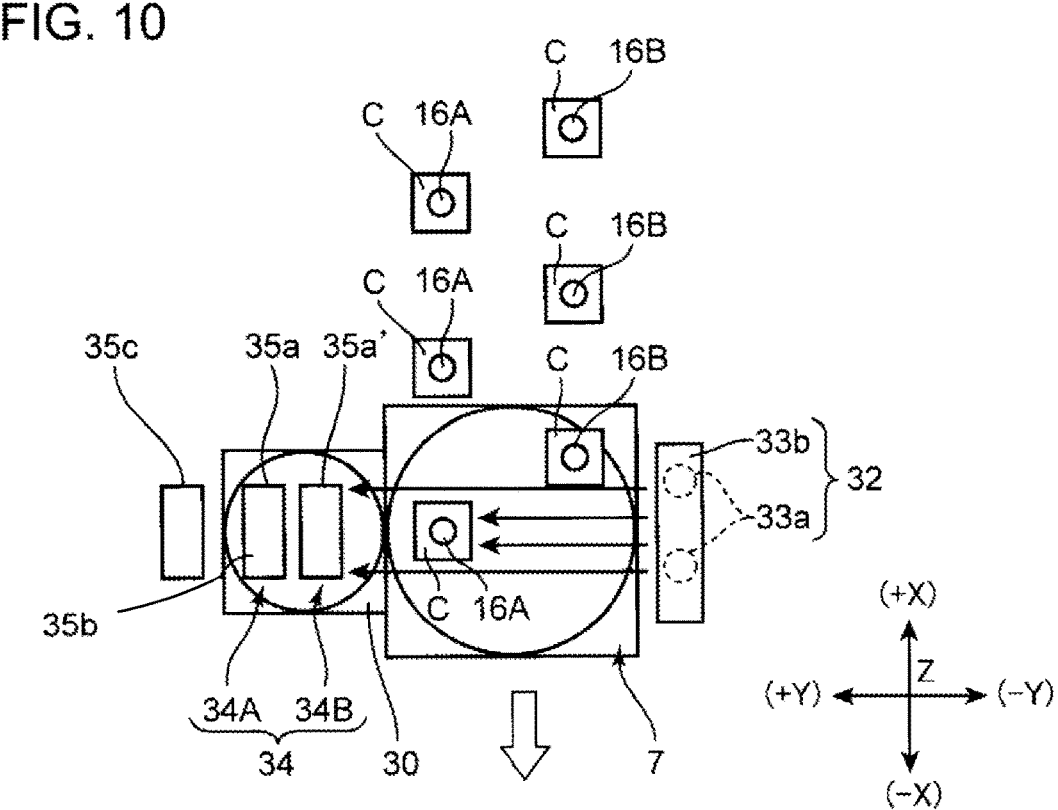
FIG. 10 is a schematic plan view of the component imaging unit.

FIG. 9 and FIG. 10 are schematic diagrams of a component imaging unit of a component mounting device according to Embodiment 3. In the component mounting device, the configuration of the second component imaging unit 8 is different from that of Embodiment 1 in terms of the following aspects, and the rest of the configuration is basically the same as the component mounting device of Embodiment 1. In the following description, a composing element which is the same as Embodiment 1 is denoted with the same reference symbol, for which a description is omitted, and primarily a difference from Embodiment 1 will be described.

The second component imaging unit 8 according to Embodiment 3 has a camera 30 that includes a CCD linear sensor (line sensor 31). This camera 30 is disposed such that the picture elements line in the Y direction, sequentially captures the projection images of one line of components C held by the respective mounting heads 16 as the head unit 6 moves in the X direction, and outputs this image data to the controller 40.

In the optical system 34, the first mirror 35a is a dedicated mirror for guiding a projection image of a holding component C of the front row head 16A out of the mounting heads 16 (this mirror 35a is called the "first mirror for the front row 35a" in this embodiment), and separate from the first mirror for the front row 35a. A first mirror 35a' constituted by a half mirror for guiding a projection image of a holding component C of the rear row head 16B (this mirror 35a' is called the "first mirror for the rear row 35a"' in this embodiment) is disposed between the first mirror for the front row 35a and the holding components C of the mounting heads 16. By this configuration, the first light-guiding portion 34A guides an image that transmits through the first mirror for the rear row 35a', out of the projection images of the component C held by the front row head 16A to an area on the front side (+Y direction side) of the line sensor 31 while reflecting the image a plurality of times using the first mirror for the front row 35a and the second mirror 35b to the fifth mirror 35e. The second light-guiding portion 34B, on the other hand, reflects a projection image of a component C held by the rear row head 16B using the first mirror for the rear row 35a', and guides the image to an area on the rear side (−Y direction side) of the line sensor 31. In other words, the light-guiding portions 34A and 34B are lined up in the Y direction, and guide the projection images of the components C held by the respective heads 16A and 16B to the camera 30 maintaining the same position in the X direction as the head unit 6 moves. In other words, in the second component imaging unit 8 according to Embodiment 3, the first component imaging position and the second component imaging position are set in the same position in the X direction.

In the component mounting device of Embodiment 3, the holding components C of the respective heads 16A and 16B move between the optical system 34 and the illumination portion 32 along the predetermined path in the X direction as the head unit 6 moves, in a state where the illumination light is being irradiated from the illumination portion 32, and by this movement, and the projection images of the components C held by the respective heads 16A and 16B are alternately captured by the camera 30.

In the component mounting device of Embodiment 3, the projection images of the holding components C of the respective heads 16A and 16B are all reflected by the first mirror for the front row 35a and form images on the line sensor 31 via the first light-guiding portion 34A, or are reflected by the first mirror for the rear row 35a' and form images on the line sensor 31 via the second light-guiding portion 34B. However since the first mirror for the front row 35a and the first mirror for the rear row 35a' are separated from each other in the Y direction, the projection image formed on the line sensor 31 via the first light-guiding portion 34A is located in the front side area of the line sensor 31, and the projection image formed on the line sensor 31 via the second light-guiding portion 34B is located in the rear side area of the line sensor 31. Furthermore, the optical path length of the first light-guiding portion 34A is set so that a focused image of the holding component C of the front row head 16A can be obtained, and the optical path length of the second light-guiding portion 34B is set so that a focused image of the holding component C of the rear row head 16B can be obtained. Therefore even if the projection image of the holding component C of the front row head 16A is guided to the camera 30 by the second light-guiding portion 34B, this projection image of the holding component C of the front row head 16A becomes out of focus and unclear. For the same reasons, even if the projection image of the holding component C of the rear row head 16B is guided to the camera 30 by the first light-guiding portion 34A, this projection image becomes out of focus and unclear. As a consequence, the image processor 44 performs processing to extract only images in the front side area of the line sensor 31, for the projection image of the holding component C of the front row head 16A, and performs processing to extract only images in the rear side area of the line sensor 31, for the projection image of the component C held by the rear row head 16B. Thereby well focused images are obtained respectively as projection images of the components C held by the respective heads 16A and 16B.

Figure 11:
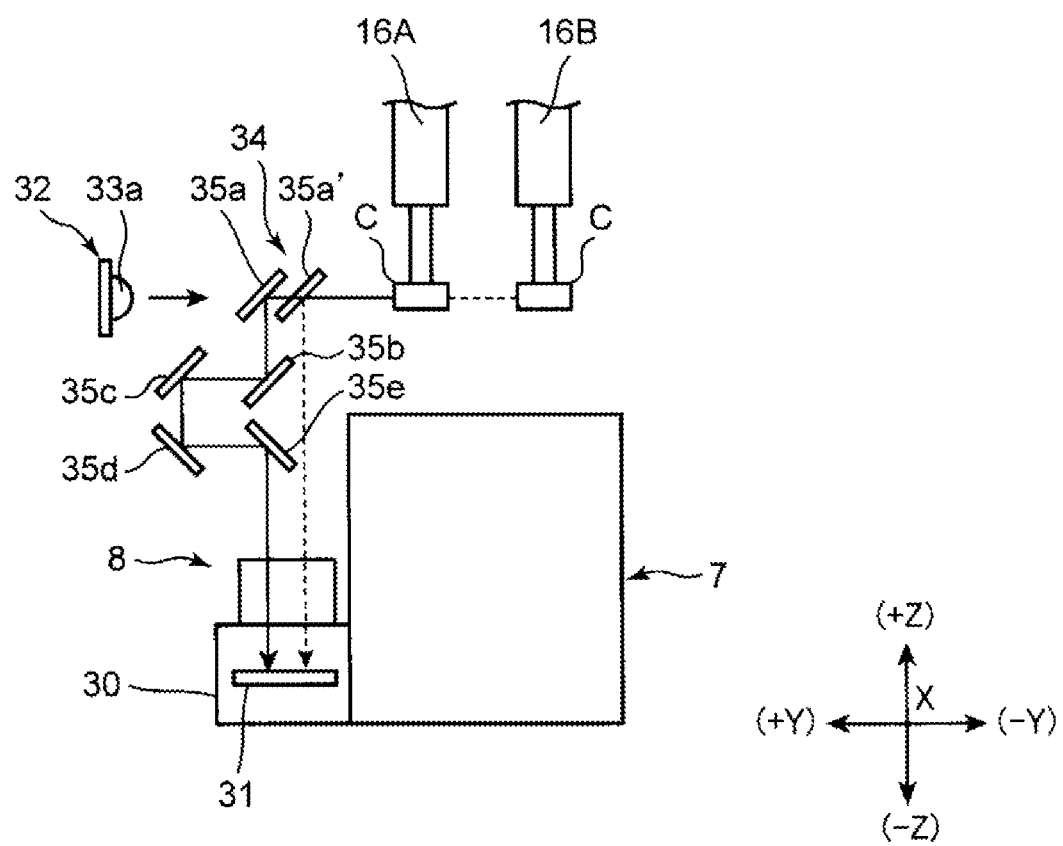
FIG. 11 is a schematic side view of a modification of the component imaging unit.

In this component mounting device, the second component imaging unit 8 is not limited to the configuration of capturing a projection image of a component C, but may capture a reflection image of a component C. FIG. 11 is an example of this embodiment.

In the second component imaging unit 8 in FIG. 11, a half mirror is used as the first mirror for the front row 35a. The illumination portion 32 irradiates illumination light from the light source 33a disposed on the front side (+Y direction side) of the first mirror for the front row 35a onto the holding components C of the respective heads 16A and 16B via the first mirror for the front row 35a and the first mirror for the rear row 35a'.

In the case of this configuration, the illumination light reflected by the holding component C of the front row head 16A, that is, the reflection image, transmits through the first mirror for the rear row 35a', and is reflected by the first mirror for the front row 35a and the second mirror 35b to the fifth mirror 35e, and is guided to the front side area of the line sensor 31 of the camera 30. The reflection image of the holding component C of the rear row head 16B is reflected by the first mirror for the rear row 35a' and is guided to the rear side area of the line sensor 31 of the camera 30. Thereby the reflection images of the components C held by the respective heads 16A and 16B are captured by the camera 30.

Embodiment 4

Figure 13:
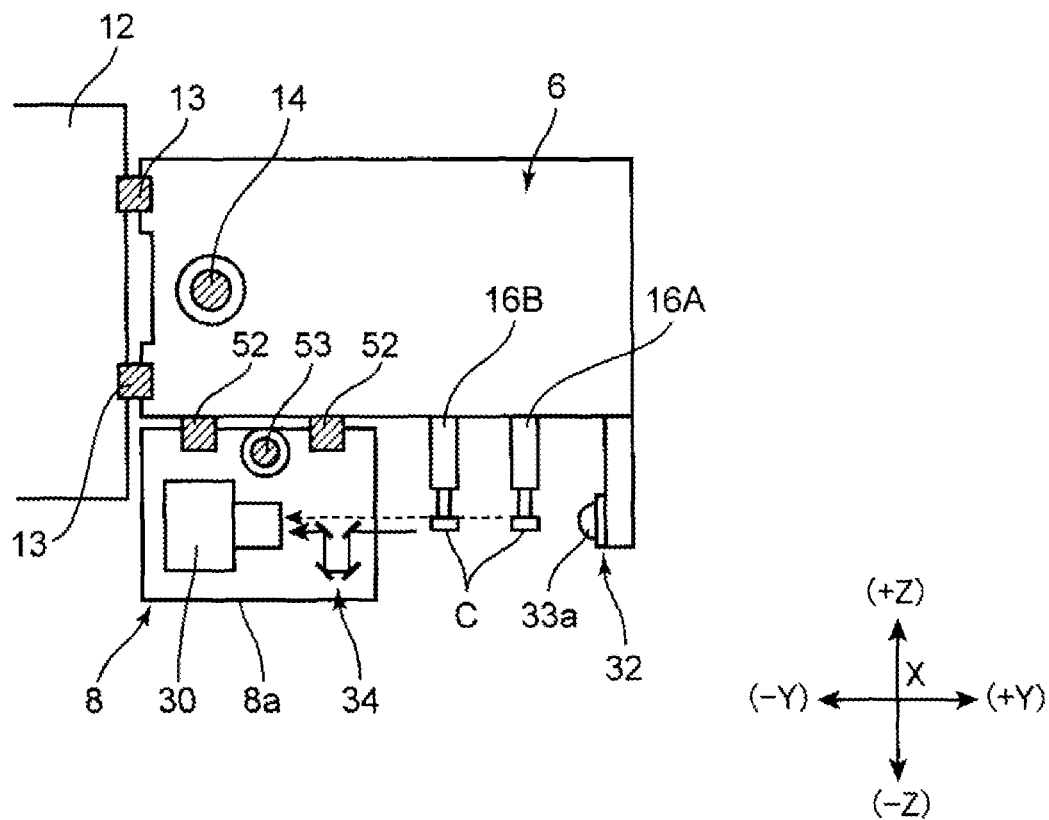
FIG. 13 is a schematic side view of a head unit and a component imaging unit.

FIG. 12 and FIG. 13 are schematic diagrams of a component mounting device according to Embodiment 4. FIG. 12 is a schematic front view of the component mounting device, and FIG. 13 is a schematic side view of the head unit 6. In this component mounting device, the second component imaging unit 8 is equipped in the head unit 6, and the rest of the configuration is basically the same as the component mounting device of Embodiment 1. In the following description, a composing element which is the same as Embodiment 1 is denoted with the same reference symbol, for which a description is omitted, and primarily a difference from Embodiment 1 will be described.

As illustrated in FIG. 12 and FIG. 13, in this component mounting device, the second component imaging unit 8 includes the camera 30, the optical system 34 and a case 8a where these composing elements are housed, and the illumination portion 32 is disposed separately from the second component imaging unit 8. The second component imaging unit 8 is disposed on the rear side (−Y direction side) of the heads 16A and 16B, and is movably supported on the bottom face of the head unit 6 via a pair of fixed rails 52 that extends in the X direction. A ball screw shaft 53, which is rotary-driven by the driving of a servo motor located outside the drawings, is screwed into the case 8a, and the servo motor is controlled by the main controller 41 via the driving controller 45, whereby the second component imaging unit 8 moves in the X direction. In this embodiment, the servo motor and the ball screw shaft 53 correspond to the moving device of the present disclosure.

The illumination portion 32 does not include the illumination mirror 33b, and a plurality of light sources 33a are secured to a mounting member that suspend from the front edge of the head unit 6, so that the illumination light is directly irradiated backward onto the components C held by the respective heads 16A and 16B. Each light source 33a is disposed in the front side of each head 16A and 16B. The camera 30 of the second component imaging unit 8 is equipped in the case 8a so as to face the front side of the device. By this configuration, the second component imaging unit 8 moves in the X direction with respect to the head unit 6 and each light source 33a is sequentially turned ON from one end in the X direction, whereby the projection images of the components C held by the respective heads 16A and 16B are captured by the camera 30. While the first light-guiding portion 34A is constructed such that the projection image of the component C held by the front row head 16A directly enters the camera 30, the second light-guiding portion 34B is constructed such that the projection image of the component C held by the rear row head 16B is reflected by a plurality of mirrors and is then guided to the camera 30. The optical path lengths of the respective light-guiding portions 34A and 34B are set such that focused images can be obtained as the projection images of the respective components C.

In the component mounting device of Embodiment 4, after the respective mounting heads 16 extract components from the component supply portions 4 and 5, the second component imaging unit 8 moves with respect to the head unit 6, as indicated by the arrows in FIG. 12, in a state where each mounting head 16 is disposed in a predetermined component imaging height position. During this movement, each light source 33a sequentially turns ON, whereby the projection images of the components C held by the respective heads 16A and 16B are captured by the camera 30.

Figure 14:
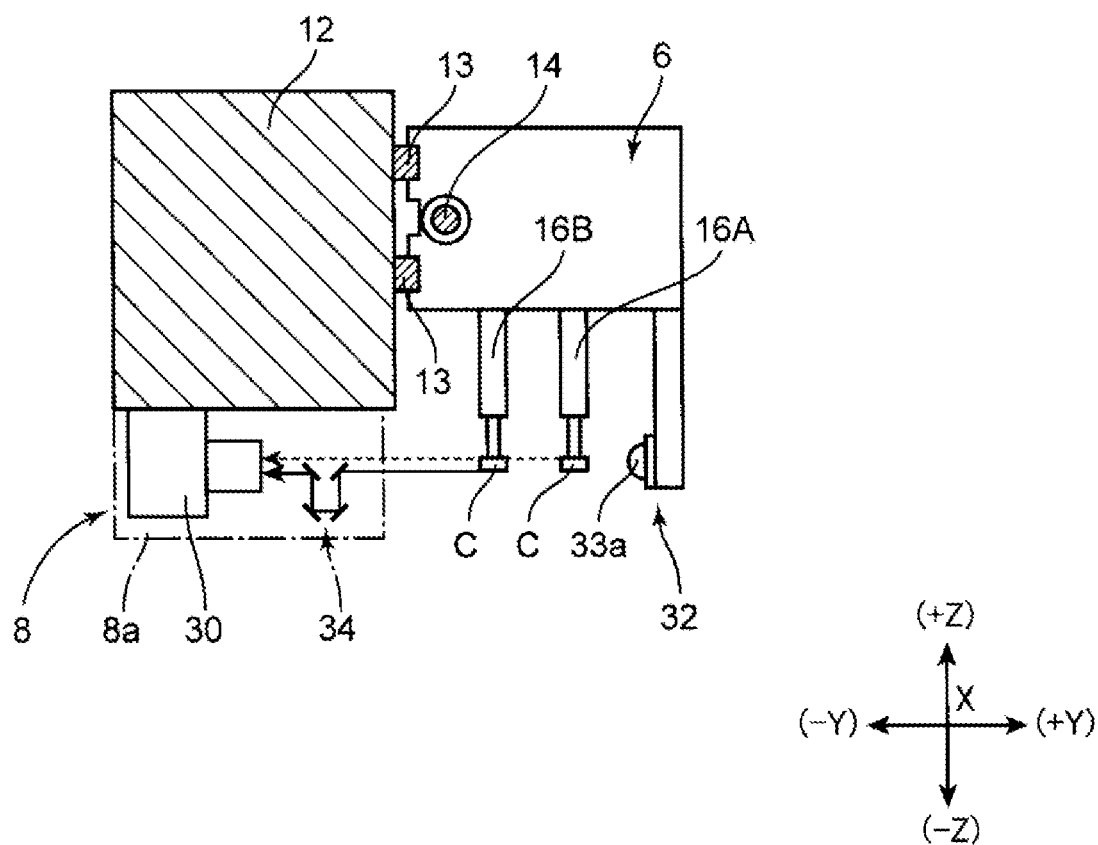
FIG. 14 is a schematic side view of a head unit, head unit support member, and a component imaging unit according to a modification of Embodiment 4.

In the example in FIG. 12 and FIG. 13, the second component imaging unit 8 is movably supported on the head unit 6, but as illustrated in FIG. 14, the second component imaging unit 8 may be fixed to an appropriate position of the unit support member 12, such as a center position in the X direction. In the case of this configuration, the head unit 6 moves in the X direction in a state where the respective mounting heads 16 are disposed in a predetermined component imaging height position, whereby the projection images of the components C held by the respective heads 16A and 16B are captured by the camera 30 during the movement. According to this configuration, a dedicated driving mechanism for moving the second component imaging unit 8 is unnecessary, and the configuration can be simplified and cost can be decreased compared with the example illustrated in FIG. 12 and FIG. 13. In this embodiment, the X axis servo motor 15 and the ball screw shaft 14 correspond to the moving device of the present disclosure.

Embodiment 5

Figure 15:
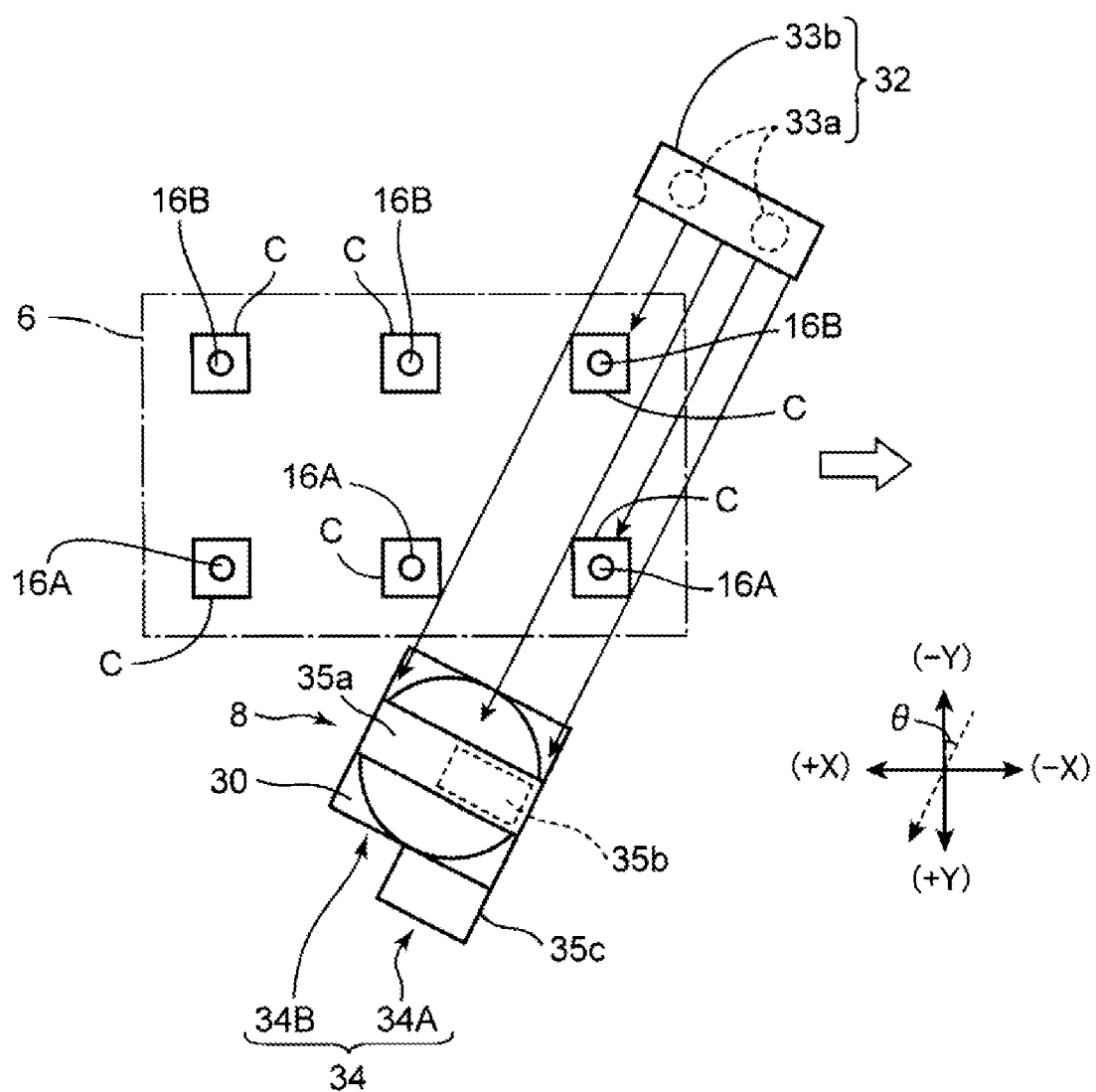
FIG. 15 is a schematic plan view of a component imaging unit equipped in a component mounting device according to Embodiment 5.

FIG. 15 illustrates a component mounting device according to Embodiment 5. FIG. 15 is a schematic plan view of the head unit 6 and the second component imaging unit 8 of the component mounting device. In the component mounting device, the configuration of the head unit 6 and the second component imaging unit 8 is different from that of Embodiment 1 in terms of the following aspects, and the rest of the configuration is basically the same as the component mounting device of Embodiment 1. In the following description, a composing element which is the same as Embodiment 1 is denoted with the same reference symbol, for which a description is omitted, and primarily a difference from Embodiment 1 will be described in detail.

In the component mounting device according to Embodiment 5, the front row heads 16A and the rear row heads 16B of the head unit 6 are aligned as illustrated in FIG. 15, that is, arranged such that the respective front row heads 16A and the respective rear row heads 16B are disposed in the same position in the X direction. The distances between the respective mounting heads 16 are set so that the mounting heads 16 shift from each other in a direction perpendicular to the direction that is a predetermined angle 8 inclined from the Y direction (corresponding to the specific direction of the present disclosure; the broken line arrow direction indicated in FIG. 15) when the mounting heads 16 are viewed from the side face in the inclined direction. Further, as illustrated in FIG. 15, the second component imaging unit 8 is constructed so as to capture the projection images of the holding components C of the respective heads 16A and 16B, while irradiating the illumination light in a direction parallel with the inclined direction. The second component imaging unit 8 of the Embodiment 5 is set in a position where the first component imaging position and the second component imaging position are in the same position in the X direction. In FIG. 15, the first component imaging unit 7 is omitted for simplification.

In the component mounting device according to Embodiment 5, unlike Embodiment 1, the mounting heads 16 are aligned while the second component imaging unit 8 is inclined in the Y direction, so that the projection images of the components C held by the heads 16A and 16B can be captured. According to this configuration, the head unit 6 can obtain focused side face images of the holding components C of all the mounting heads 16, just like Embodiment 1, even if the front row head 16A and the rear row head 16B are aligned.

Embodiment 6

Figure 16:
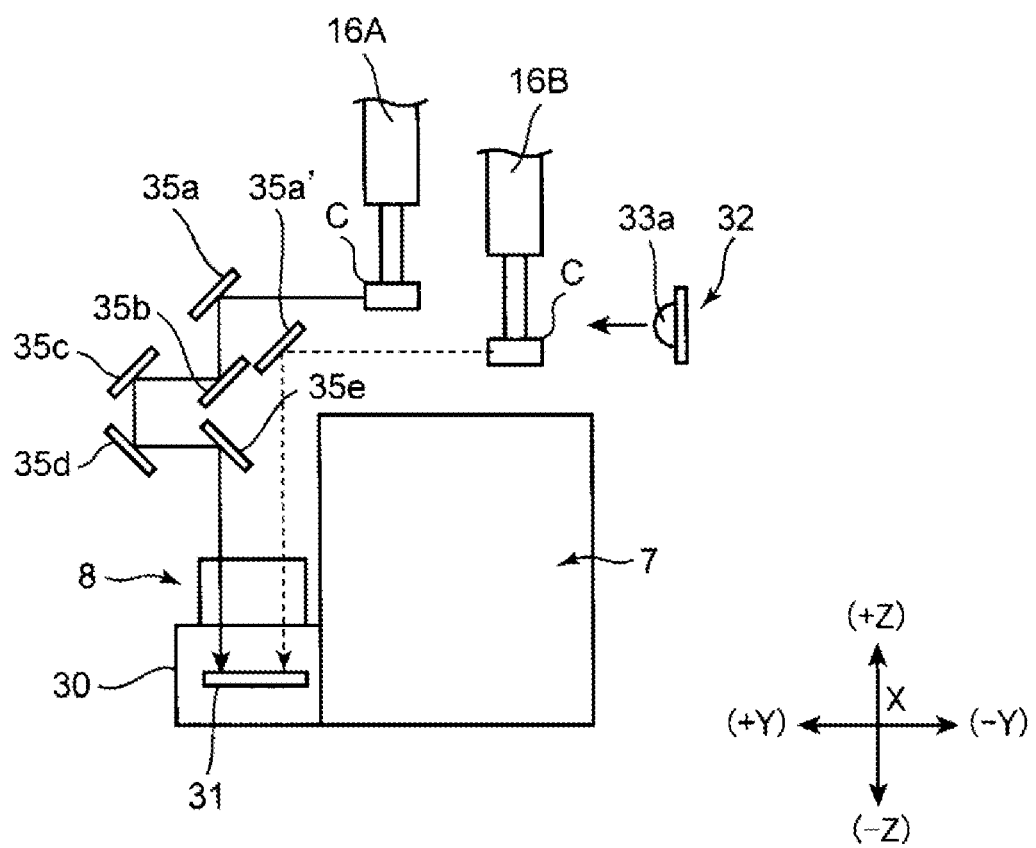
FIG. 16 is a schematic side view of a component imaging unit equipped in a component mounting device according to Embodiment 6.

FIG. 16 is a schematic diagram of a component imaging unit of a component mounting device according to Embodiment 6. In this component mounting device, the configuration of the second component imaging unit 8 is different from that of Embodiment 3 (FIG. 9 and FIG. 10) in terms of the following aspects, and the rest of the configuration is basically the same as the component mounting device of Embodiment 3. In the following description, a composing element which is the same as Embodiment 3 is denoted with the same reference symbol, for which a description is omitted, and primarily a difference from Embodiment 3 will be described in detail.

In the component mounting device according to Embodiment 6, the front row heads 16A and the rear row heads 16B are equipped in the head unit 6 in an aligned state, that is, in a state where the respective front row heads 16A and the respective rear row heads 16B are arranged in the same position in the X direction, just like the configuration illustrated in FIG. 15.

In the second component imaging unit 8, the first mirror for the rear row 35a' of the second light-guiding portion 34B is located in a position lower than the first mirror for the front row 35a of the first light-guiding portion 34A. In other words, in the second component imaging unit 8, the first component imaging position is set to a position that is higher than the second component imaging position.

In this component mounting device, when the components C are imaged, the front row heads 16A and the rear row heads 16B are controlled to have mutually different height positions so that a projection image of a holding component C of the front row head 16A is reflected by the first mirror for the front row 35a, while a projection image of a holding component C of the rear row head 16B is reflected by the first mirror for the rear row 35a', as illustrated in FIG. 16. In other words, the main controller 41 controls the imaging height positions of the front row heads 16A and the rear row heads 16B, so that the height position of a holding component C of the front row head 16A becomes the same as the height position of the first mirror for the front row 35a, and the height position of a holding component C of the rear row head 16B becomes the same as the height of the first mirror for the rear row 35a'. By the head unit 6 being controlled in this state so that the head unit 6 moves in the X direction with respect to the second component imaging unit 8, the projection images of one line of holding components C of the heads 16A and 16B, which are adjacent to each other in the front-back direction (Y direction), are simultaneously captured by a line sensor 31 along with this movement.

According to this configuration of Embodiment 6, a focused side face image can be obtained for the holding components C of all the mounting heads 16 respectively, even if the front row heads 16A and the rear row heads 16B are aligned.

The component mounting devices of the embodiments described above are examples of the preferred embodiments of the component mounting device according to the present disclosure (component mounting device to which the component imaging device according to the present disclosure is applied), and a concrete configuration thereof can be modified without departing from the true spirit and scope of the disclosure.

For example, a configuration combining each configuration of Embodiment 1 to Embodiment 6 may be used. In concrete terms, the filter device of Embodiment 2 may be used for Embodiment 3 to Embodiment 6. According to this configuration, images with better contrast can be obtained as images of components C held by the heads 16A and 16B which are adjacent to each other.

In the optical system 34 of the second component imaging unit 8 in each embodiment, images of the holding components C of the mounting head 16 are reflected primarily by the mirrors, and are guided to the camera 30, but prisms may be used or mirrors and prisms may be combined.

In each embodiment illustrated in FIG. 1 to FIG. 11, FIG. 15 and FIG. 16, the first and second component imaging units 7 and 8 are disposed only between the trays 5a and 5b on the base 1, but similar component imaging units 7 and 8 may be disposed for the component supply portion 4 as well.

In this case, the component supply portion 4 is divided into two component supply portions, which are separated by a gap in the X direction, and the extra component imaging units having the same configuration as the component imaging units 7 and 8 are disposed in the position between these two component supply portions on the base 1. The extra component imaging units are disposed symmetrically with respect to the component imaging units 7 and 8, that is, in a state where the component imaging units 7 and 8 are rotated 180° in the R direction. According to this configuration, even if the last component that is suctioned just before the head unit 6 moves onto the substrate 3 for mounting components is a chip component, that is, even if the last component is extracted from the component supply portion 4 by the front row heads 16A or the rear row heads 16B, the head unit 6 can be moved to the extra component imaging units disposed on the component supply portion 4 side so as to recognize the component holding state by each head 16A and 16B. Thereby the moving distance of the head unit 6 can be decreased, and the mounting cycle time can be decreased.

In each embodiment, the head unit 6 is constituted by the plurality of mounting heads 16 which are arranged in the front row and the rear row, but the present disclosure can be applied to the case of three or more rows of mounting heads 16. In this case, the rows adjacent to each other form the relationship of the front row and the rear row described above, hence a functional effect equivalent to the component mounting device (component imaging unit) of Embodiments 1 to 6 can be demonstrated by applying the configuration of these embodiments.

In each embodiment, focused side face images are obtained for the holding components C of all the mounting heads 16, but obtaining an image of a holding component C may be omitted if it is not necessary to obtain the side face image thereof. In this case, after components are extracted, the height of the mounting head 16 holding a component of which image is not obtained is controlled to be higher than the imaging height position, so that this holding component C is located higher to be removed from the optical path of the optical system 34, from the illumination portion 32 to the first mirrors 35a and 35a'.

The present disclosure described above is summarized as follows.

A component imaging device according to an aspect of the present disclosure has: a head unit that has a first head row that includes a plurality of vertically movable heads arranged in a row in a first direction, and a second head row that includes a plurality of vertically movable heads arranged in a row in the first direction and that is arranged in a second direction perpendicular to the first direction with respect to the first head row; an imaging unit that images components held by the respective heads from a position on one side of the second direction; an illumination device for irradiating illumination light for imaging on the components held by the heads; a moving device for relatively moving the head unit with respect to the imaging unit along a predetermined path which is parallel with the first direction, in order to image the components held by the heads; and an imaging control device for performing control related to the component imaging operation, wherein the imaging unit includes an image sensor and an optical system that guides light from a component held by the head for generating an image of the component, to the image sensor. The optical system includes: a first light-guiding portion that guides, to the image sensor, light from a component that has reached a predetermined first component imaging position, out of the components held by the respective heads of the first head row, as the head unit relatively moves along the predetermined path with respect to the imaging unit; and a second guiding portion that guides, to the image sensor, light from a component that has reached a predetermined second component imaging position, out of the components held by the respective heads of the second head row. An optical path length from the first component imaging position to the image sensor is set for the first light-guiding portion so as to obtain a focused image of a component held by a head of the first head row. An optical path length from the second component imaging position to the image sensor is set for the second light-guiding portion so as to obtain a focused image of a component held by a head of the second head row. The imaging control device controls height positions of the heads and an exposure timing of the image sensor based on the respective component imaging positions, so that when the head unit relatively moves along the predetermined path with respect to the imaging unit, light from a component held by a head of the first head row is guided to the image sensor by the first light-guiding portion, and light from a component held by a head of the second head row is guided to the image sensor by the second light-guiding portion.

According to this component imaging device, a focused image of a component held by each head of the first head row is obtained since the light from the component is guided to the image sensor by the first light-guiding portion of the optical system. On the other hand, a focused image of a component held by each head of the second head row is also obtained since the light from the component is guided to the image sensor by the second light-guiding portion of the optical system. Therefore equally good focused images can be obtained for any holding components of both head rows. In the description, "light from a component" refers to both light to form a projection image of the component and light to form a reflection image of the component.

In concrete terms, the heads of the first head row and the heads of the second head row are arranged to be shifted from each other in a direction perpendicular to a specific direction crossing the first direction when viewed from the specific direction. The first component imaging position and the second component imaging position are set at the same height, and the imaging unit images components held by the heads of the respective head rows from one side of the specific direction. In this case, the specific direction may be a direction perpendicular to the first direction, that is the second direction, or may be a direction inclined from the first direction.

In this component imaging device, the head unit and the imaging unit are relatively moved in the first direction in a state where all the heads are disposed in the same height position. Thereby the focused images of the components held by all the heads from the side direction can be obtained.

Another concrete configuration is that the respective heads of the first head row and the respective heads of the second head row are disposed in the same position when viewed from the second direction. The first component imaging position is set to a position higher than the second component imaging position. The imaging unit images components held by the heads of the respective head rows from one side of the specific direction.

In this component imaging device, the head unit and the imaging unit are relatively moved in the first direction in a state where the respective heads of the first head row and the respective heads of the second head row are disposed in mutually different height positions. Thereby the images of the components held by the heads of the respective head rows from the side direction can be obtained. According to this configuration, focused images of the components held by all the heads from the side direction can be obtained even if the structure is the same as a conventional head unit, where the heads of the respective head rows are aligned.

In the component imaging device, it is preferable that the first light-guiding portion and the second light-guiding portion allow mutually different areas of the image sensor to simultaneously receive light from two components held by a pair of heads which belong to mutually different head rows and are adjacent to each other.

According to this configuration, two components, held by a pair of heads that belong to mutually different head rows and are adjacent to each other can be simultaneously imaged in a focused state, and hence components held by the heads of the respective head rows can be efficiently imaged.

In the component imaging device, it is preferable that when a component held by a head of the first head row is defined as a first component and a component held by a head of the second head row is defined as a second component, the illumination device irradiates illumination light onto a pair of a first component and a second component which are adjacent to each other, and the component imaging device further comprises a filter device for removing light having specific wavelength components in an optical path from the illumination device to the image sensor, so that the light from the first component that enters the image sensor and the light from the second component that enters the image sensor include mutually different wavelength components.

According to this component imaging device, a phenomenon where the light from the first component and the light from the second component adjacent to the first component influence each other, and where the contrast of each component image drops, can be suppressed.

In concrete terms, the illumination device includes a first light source that irradiates illumination light having a first wavelength onto the first component, and a second light source that irradiates illumination light having a second wavelength, which is different from the first wavelength, onto the second component, and the filter device includes at least one of a first filter and a second filter, where the first filter removes light having the second wavelength components so that the light from the first component that enters the image sensor does not include the light components having the second wavelength, and the second filter removes light having the first wavelength components so that the light from the second component that enters the image sensor does not include the light components of the first wavelength.

According to this configuration, the light from the first component and the light from the second component adjacent to the first component include only mutually different wavelength components, and hence the contrast of the respective component images become good, and high quality component images of the first component and the second component can be obtained.

In this case, the first filter includes at least one of a first upstream side filter that removes light components having a second wavelength out of the illumination light having a first wavelength irradiated from the first light source onto the first component, and a first downstream side filter that removes light components having the second wavelength out of the light from the first component, and the second filter includes at least one of a second upstream side filter that removes light components having a first wavelength out of the illumination light having a second wavelength irradiated from the second light source onto the second component, and a second downstream side filter that removes the light components having the first wavelength out of the light from the second component.

According to this configuration, the contrast of each component image further improves and even higher quality component images can be obtained as the component images of the first component and the second component.

A component mounting device according to an aspect of the present disclosure is a component mounting device that extracts components from a component supply portion and mounts the components on a substrate, comprising: any of the component imaging devices described above; and a mounting control device for mounting components held by the respective heads of the head unit on a substrate by controlling the moving device of the component imaging device.

According to this component mounting device, components can be mounted efficiently by equipping many heads to a head unit while limiting the size of the head unit from becoming large, and the components held by the heads of the respective head rows can be imaged and recognized from the side with equally good quality.

INDUSTRIAL APPLICABILITY

As described above, the present disclosure is a technique that is applied to a component mounting device, and when a plurality of heads are divided into a plurality of rows and are equipped on the head unit in this state, this technique allows imaging the components held by the respective heads from the side direction with equally good quality. Therefore the present disclosure is particularly useful in the field of the manufacture of component mounting substrates.

The invention claimed is:

1. A component imaging device, comprising:
a head unit having a first head row including a plurality of vertically movable heads arranged in a row in a first direction, and a second head row including a plurality of vertically movable heads arranged in a row in the first direction and said second head row is disposed away from the first head row with a predetermined distance in a direction parallel to the first direction;
a first imaging unit that includes a first image sensor facing upward and images components held by the respective heads from below;
a second imaging unit that is disposed on a side of the first imaging unit and images the components held by the respective heads from one side of a second direction perpendicular to the first direction;
an illumination device for irradiating illumination light in the second direction for imaging on the components held by the heads;
a moving device for relatively moving the head unit along a predetermined path which is parallel with the first direction and is positioned above the first imaging unit, in order to image the components held by the heads; and
an imaging control device for performing control related to the component imaging operation, wherein
the heads of the first head row and the heads of the second row are arranged to be shifted from each other in the first direction when viewed from the second direction,
the illumination device allows the illumination light to have an illumination width adaptable to irradiate two components held by a pair of heads which belong to mutually different head rows and are adjacent to each other in the first direction when viewed from the second direction, and
the second imaging unit includes a second image sensor that is disposed to face upward and to be adjacent to the first image sensor in the second direction, and an optical system that guides light from a component held by the head to the second image sensor for generating an image of the component,
the optical system includes: a first light-guiding portion that guides, to the second image sensor light from a component that has reached a predetermined first component imaging position located above the first imaging unit, out of the components held by the respective heads of the first head row, as the head unit relatively moves along the predetermined path with respect to the first imaging unit; and a second guiding portion that guides, to the second image sensor, light from a component that has reached a predetermined second component imaging position located above the first imaging unit, out of the components held by the respective heads of the second head row,
the first light-guiding portion includes a mirror that is disposed above the second image sensor and reflects light from the component downward so as to guide the light to the second image sensor, and an optical path length from the first component imaging position to the second image sensor is set for the first light-guiding portion so as to obtain a focused image of a component held by a head of the first head row,
the second light-guiding portion includes a mirror that is disposed above the second image sensor and reflects light from the component downward so as to guide the light to the second image sensor, and an optical path length from the second component imaging position to the second image sensor is set for the second light-guiding portion so as to obtain a focused image of a component held by a head of the second head row,
the first component imaging position and the second component imaging position are set at a same height and are positions where the two components held by the pair of heads which belong to the mutually different head rows and are adjacent to each other in the first direction when viewed from the second direction are located above the first imaging unit,
the first light-guiding portion and the second light-guiding portion allow mutually different areas of the second image sensor to simultaneously receive light from the two components held by the pair of heads which belong to the mutually different head rows and are adjacent to each other in the first direction when viewed from the second direction, and
the imaging control device controls height positions of the heads and exposure timings of the respective imaging units based on the respective component imaging positions, so that when the head unit relatively moves along the predetermined path with respect to the first imaging unit, a bottom face image of a component held by a head of the first head row is imaged by the first imaging unit and a side image of the component is imaged by the second imaging unit by the first light-guiding portion guiding the light from the component to the second image sensor, while a bottom face image of a component held by a head of the second head row is imaged by the first imaging unit and a side image of the component is imaged by the second imaging unit by the second light-guiding portion guiding the light from the component to the second image sensor, wherein
the images of the components held by their respective heads are captured by one or more cameras.

2. The component imaging device according to claim 1, wherein
when a component held by a head of the first head row is defined as a first component and a component held by a head of the second head row is defined as a second component,
the component imaging device further comprises a filter device for removing light having specific wavelength components in an optical path from the illumination device to the second image sensor, so that the light from the first component that enters the second image sensor and the light from the second component that enters the second image sensor include mutually different wavelength components.

3. The component imaging device according to claim 2, wherein
the illumination device includes a first light source that irradiates illumination light having a first wavelength onto the first component, and a second light source that irradiates illumination light having a second wavelength, which is different from the first wavelength, onto the second component, and
the filter device includes at least one of a first filter and a second filter, where the first filter removes light having the second wavelength components so that the light from the first component that enters the second image sensor does not include the light components having the second wavelength, and the second filter removes light having the first wavelength components so that the light from the second component that enters the second image sensor does not include the light components of the first wavelength.

4. The component imaging device according to claim 3, wherein
the first filter includes at least one of a first upstream side filter that removes light components having a second wavelength out of the illumination light having a first wavelength irradiated from the first light source onto the first component, and a first downstream side filter that removes light components having the second wavelength out of the light from the first component, and
the second filter includes at least one of a second upstream side filter that removes light components having a first wavelength out of the illumination light having a second wavelength irradiated from the second light source onto the second component, and a second downstream side filter that removes the light components having the first wavelength out of the light from the second component.

5. The component imaging device according to claim 1, wherein
the illumination device includes an illumination portion that irradiates illumination light for imaging by the second imaging unit,
the illumination portion is disposed in a position on a side of the first imaging unit in the second direction that is on a same side as the mirror, and
the mirror reflects reflected light, which has been irradiated from the illumination portion to the component and reflected by the component, so as to guide the reflected light to the second image sensor.

6. The component imaging device according to claim 1, wherein
the illumination device includes an illumination portion that irradiates illumination light for imaging by the second imaging unit,
the illumination portion is disposed in a position on a side of the first imaging unit in the second direction that is on an opposite side of the mirror, and
the mirror reflects projected light of the component resulting from irradiation onto the component by the illumination portion, so as to guide the projected light to the second image sensor.

7. A component mounting device that extracts components from a component supply portion and mounts the components on a substrate, comprising:
the component imaging device according to claim 1; and
a mounting control device for mounting components held by the respective heads of the head unit on a substrate by controlling the moving device of the component imaging device.

* * * * *